(12) United States Patent
Altarac et al.

(10) Patent No.: US 9,486,250 B2
(45) Date of Patent: Nov. 8, 2016

(54) LATERAL PLATE

(71) Applicant: Mastros Innovations, LLC, Henderson, NV (US)

(72) Inventors: Moti Altarac, Irvine, CA (US); Joey Reglos, Lake Forest, CA (US); Michael Schneier, Las Vegas, NV (US); Brian Stuart Grossman, Camarillo, CA (US); Michael Davis, Henderson, NV (US); Dale Lawrence Leibert, Moorpark, CA (US); John Fredrick Stephani, Soquel, CA (US)

(73) Assignee: Mastros Innovations, LLC., Henderson, NV (US)

( * ) Notice: Subject to any disclaimer, the term of this patent is extended or adjusted under 35 U.S.C. 154(b) by 56 days.

(21) Appl. No.: 14/184,902

(22) Filed: Feb. 20, 2014

(65) Prior Publication Data
US 2015/0230831 A1 Aug. 20, 2015

(51) Int. Cl.
*A61B 17/80* (2006.01)
*A61B 17/70* (2006.01)

(52) U.S. Cl.
CPC ....... *A61B 17/7059* (2013.01); *A61B 17/8023* (2013.01); *A61B 17/8047* (2013.01); *A61B 17/8009* (2013.01)

(58) Field of Classification Search
CPC .......... A61B 17/8009; A61B 17/8019; A61B 17/8023; A61B 17/8033; A61B 17/8047; A61B 17/8004
USPC .......... 606/294, 293, 290, 289, 282
See application file for complete search history.

(56) References Cited

U.S. PATENT DOCUMENTS

| 5,364,399 | A | 11/1994 | Lowery et al. |
| 5,549,612 | A | 8/1996 | Yapp et al. |
| 5,616,142 | A | 4/1997 | Yuan et al. |
| 5,616,144 | A | 4/1997 | Yapp et al. |
| 6,045,552 | A | 4/2000 | Zucherman et al. |
| 6,139,550 | A | 10/2000 | Michelson |
| 6,398,783 | B1 | 6/2002 | Michelson |
| 6,599,290 | B2 | 7/2003 | Bailey et al. |
| 6,602,255 | B1 | 8/2003 | Campbell et al. |
| 6,626,907 | B2 | 9/2003 | Campbell et al. |

(Continued)

FOREIGN PATENT DOCUMENTS

| EP | 1520545 B1 | 11/2006 |
| EP | 1429675 B1 | 10/2007 |

(Continued)

*Primary Examiner* — Eduardo C Robert
*Assistant Examiner* — Julianna N Harvey
(74) *Attorney, Agent, or Firm* — Rimas Lukas

(57) ABSTRACT

A bone plate system is provided. The system includes two or more fastener locks stacked on top of each other and located between two holes in a plate adapted to receive bone fasteners. An actuator is provided between the locks. As the actuator is advanced, the locks are moved sequentially into position, firstly, to prevent one or more bone fasteners from backing out of the plate while permitting the fasteners to angulate and, secondly, to lock the angulation of the bone fasteners while still providing back out protection in situ. An expandable bone plate having a top plate interconnected to a bottom plate by a rack and pinion is provided. The rotation of the pinion with a driver lengthens or shortens the plate incrementally for custom length adjustment. The length is fixed in position with the simple removal of the driver and no further step is required to lock the plate length.

19 Claims, 19 Drawing Sheets

(56) References Cited

U.S. PATENT DOCUMENTS

| | | |
|---|---|---|
| 6,652,525 B1 | 11/2003 | Assaker et al. |
| 6,695,846 B2 | 2/2004 | Richelsoph et al. |
| 7,175,623 B2 | 2/2007 | Thramann et al. |
| 7,186,254 B2 | 3/2007 | Dinh et al. |
| 7,220,263 B2 | 5/2007 | Cordaro |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,686,806 B2 | 3/2010 | Rhyne |
| 7,740,630 B2 | 6/2010 | Michelson |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,887,547 B2 | 2/2011 | Campbell et al. |
| 2002/0120270 A1 | 8/2002 | Trieu et al. |
| 2003/0093082 A1 | 5/2003 | Campbell et al. |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1* | 9/2006 | Doubler ............ A61B 17/8042 606/293 |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |
| 2006/0287653 A1 | 12/2006 | Rhyne |
| 2007/0083203 A1 | 4/2007 | Ribeiro |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |

(56) References Cited

U.S. PATENT DOCUMENTS

| | | |
|---|---|---|
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1 | 7/2009 | Sanders et al. |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0042159 A1 | 2/2010 | Butler |
| 2010/0049256 A1 | 2/2010 | Jeon et al. |
| 2010/0069968 A1 | 3/2010 | Assaker et al. |
| 2010/0234897 A1 | 9/2010 | Fisher et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0230885 A1* | 9/2011 | Weiner ............... A61B 17/8009 606/71 |
| 2014/0148860 A1* | 5/2014 | Rinner ............... A61B 17/8042 606/289 |

FOREIGN PATENT DOCUMENTS

| | | |
|---|---|---|
| EP | 1847229 A2 | 10/2007 |
| WO | 2006076422 A2 | 7/2006 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

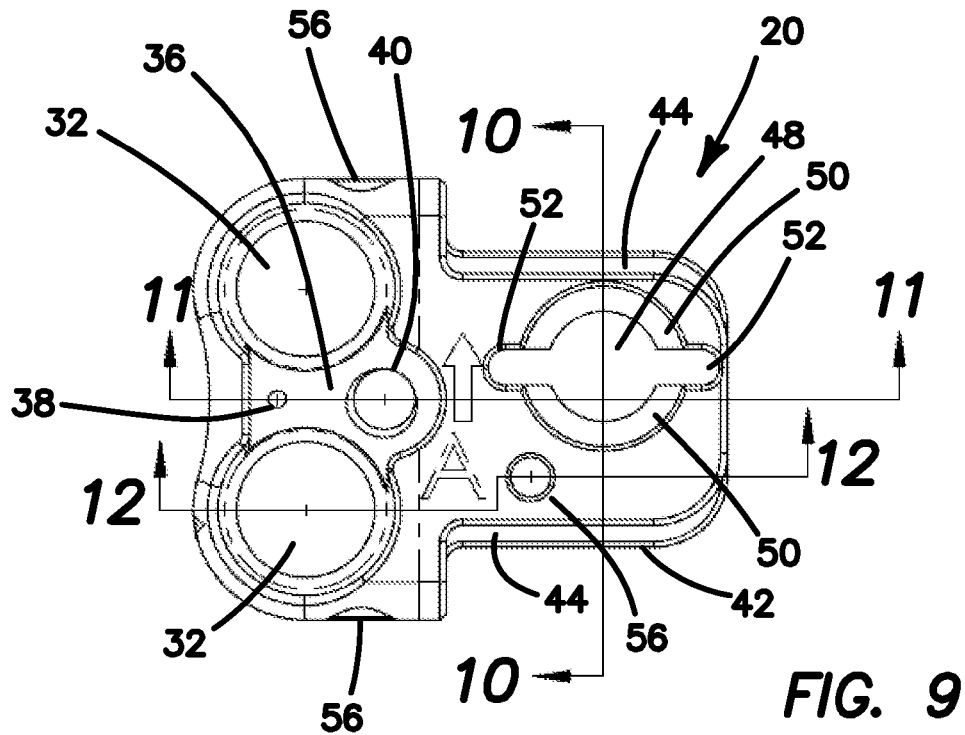
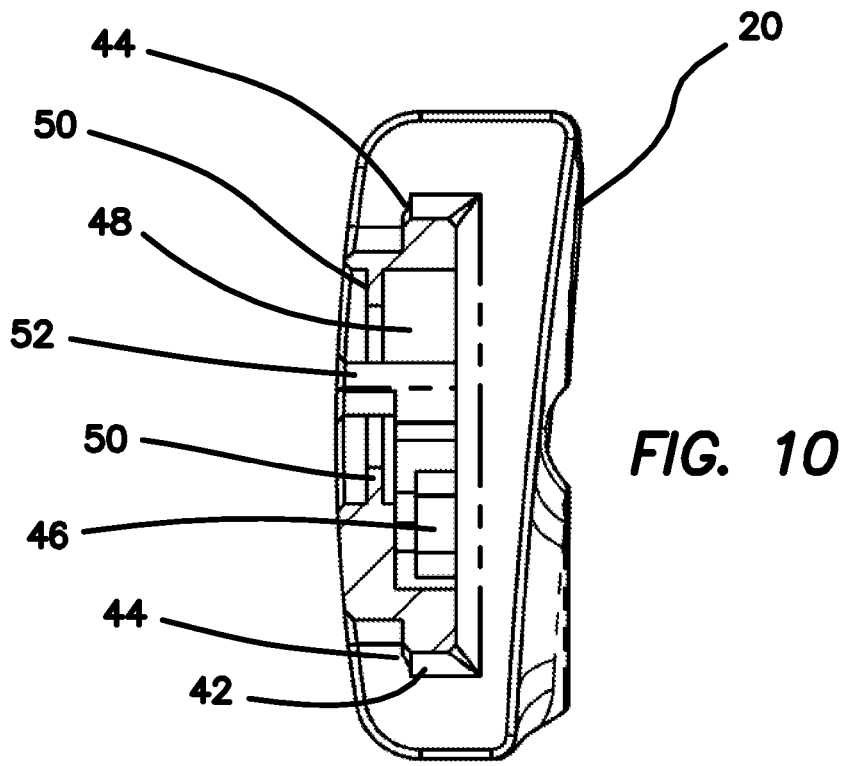

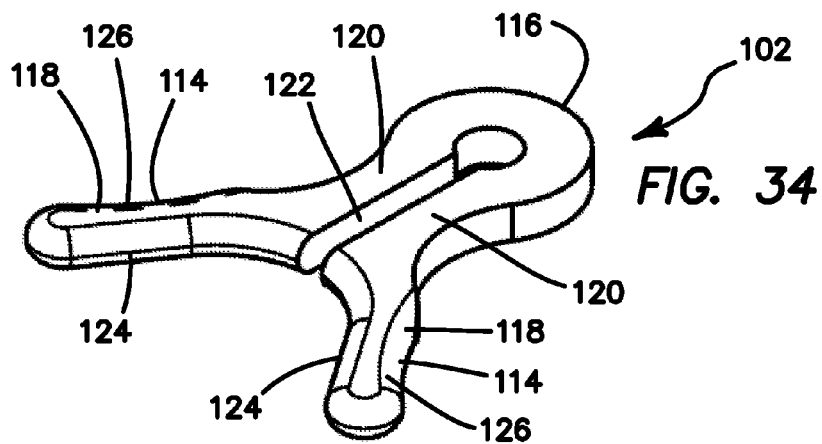
FIG. 34
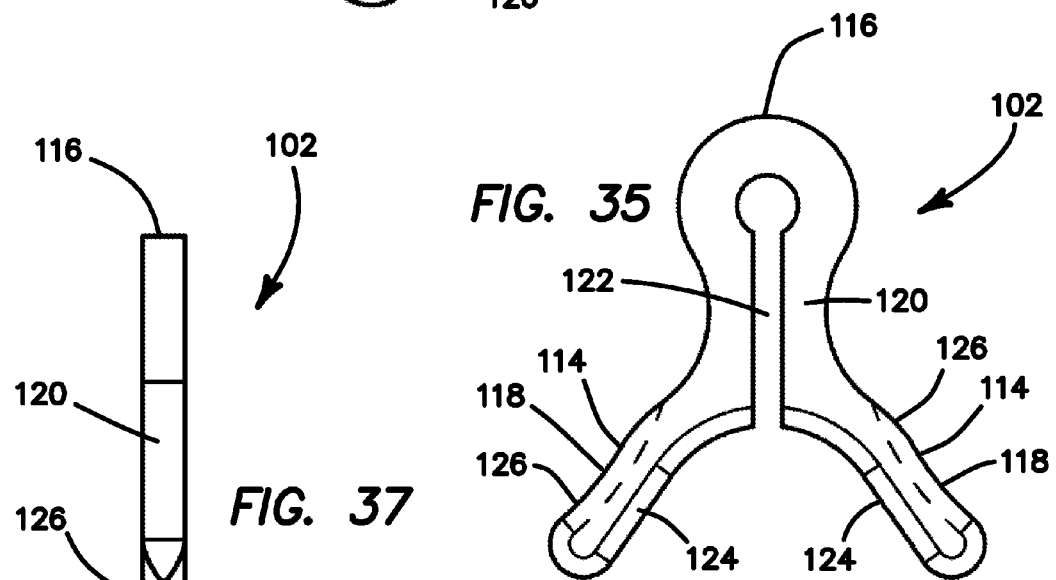
FIG. 37
FIG. 35
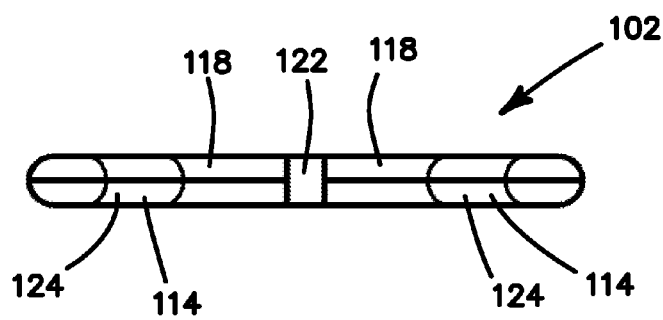
FIG. 36

LATERAL PLATE

FIELD OF THE INVENTION

This invention relates to bone fixation plates and, more particularly, to fixation plates for the spine that are expandable and to fixation plates that resist the backing out of associated bone fasteners.

BACKGROUND OF THE INVENTION

Spinal bone plates are used for a variety of conditions to immobilize, stabilize or align cervical vertebrae. For example, after a spinal fusion surgery, bone plates are used to add strength and rigidity to the adjoined vertebrae. Also, plates secure vertebrae together where an intervening vertebra has been removed or replaced. In other cases, spinal bone plates are used to correct instability in the spine caused by trauma, tumors, advanced degenerative discs, infection or congenital or acquired deformities.

A typical spinal bone plate includes an elongated rectangular plate that spans the distance between two or more vertebrae. The plate is curved to match the natural curvature of the spine at the location to which it is attached and bone screws are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Thereby, the plate bridges two vertebral bodies. More vertebrae may be connected with a longer plate and a corresponding increased number of bone screw apertures and bone screws inserted therethrough at the intervening vertebral levels.

Spinal stabilization techniques can employ bone plates on the posterior, anterior, lateral, postero-lateral, and antero-lateral portions of a spinal column to provide fixation of the spinal column for the repair of injured or diseased vertebrae, intervertebral discs and other elements of the spinal column. Holes are drilled into the vertebral bodies or self-tapping screws are employed. The plate is properly aligned on the vertebrae. Proper alignment of the plate includes selecting the correct spacing between the upper bone screws and the lower bone screws. If fixed-length plates are employed, alignment includes selecting the plate with the correct length. Variable-length plates may also be employed in which an upper portion of the plate moves longitudinally relative to a lower portion for custom length adjustment. Mounting screws are inserted through the plate and the plate is carefully and firmly attached to the bone. Sometimes fusion is accompanied by a discectomy in which a herniated disc is removed and a graft device is placed between the vertebral bodies to assist in fusion across levels. With the plate in position, the vertebrae are held by the plate in desired spatial relationships and orientations relative to each other, pressure is removed from the nerve roots and pain caused by the herniated disc or other condition is relieved.

Over time, the interface between the screws and the bone may present some problems of stability. Due to the anatomical structure of the spine and the extreme anatomical forces that are brought to bear on the skeleton and transmitted to the spine, the screws securing the plate to the spine may vibrate or toggle out of position. Also, the degeneration of vertebral bone quality may result in the screws loosening or becoming dislodged. As a result, bone screws securing the plate to the spine may move or back out of the vertebral body and plate.

Therefore, there is a need to provide a new and improved bone plate that resists fasteners, such as bone screws, from backing out of the plate and also from being loosened with respect to the plate before migrating out. Not only an improved and effective fastener retaining mechanism is required, but also, an improved expandable plate that allows for small-increment variability in its length. A properly aligned plate as a result of custom length adjustment will improve force distribution and reduce fastener migration. Furthermore, there is a need for the spinal plate to withstand anatomical forces and be easily implanted. The screw-retaining mechanism must be easily activated by the surgeon, and also, the variable length adjustment must be easily accomplished without multiple steps. This invention, as described in the detailed description, sets forth an improved spinal plate system with anti-back out protection and variable length adjustment that meets these needs.

SUMMARY OF THE INVENTION

According to one aspect of the invention, a bone plate system is provided. The bone plate system includes a plate having at least one hole configured to receive a bone fastener for attaching the plate to bone. The plate has a top surface and a bottom surface interconnected by a side surface. An actuator is located adjacent to the at least one hole. The actuator has a proximal end, a distal end, a longitudinal axis and an outer surface. In a cross section of the actuator taken perpendicular to the longitudinal axis, the outer surface of the actuator defines a shape having a length defined from its center to its perimeter. The length increases in progressively proximal cross sections perpendicular to the longitudinal axis. The actuator is connected to the plate such that the actuator moves relative to the top surface of the plate. The plate system includes at least two locks stacked on top of each other and located between the actuator and the at least one hole. Each lock has at least one actuator-facing surface and at least one fastener-facing surface. The at least two locks are connected to the plate such that at least a portion of each lock is movable relative to the plate. The actuator-facing surface faces the actuator and the fastener-facing surface faces the at least one hole. Movement of the actuator in a first direction relative to the plate moves at least a portion of each lock laterally closer to the at least one hole and moves the at least two locks consecutively with respect to each other.

According to another aspect of the invention, a bone plate system is provided. The bone plate system includes a plate having at least one hole configured to receive a bone fastener for attaching the plate to bone. The plate has a top surface and a bottom surface interconnected by a side surface. The bone plate system includes at least one fastener having a head at a proximal end and a bone-engaging portion distal to the head. The bone-engaging portion extends to a distal end. The fastener is disposed inside at least one hole of the plate such that the head is substantially seated inside the hole and the bone-engaging portion extends from the bottom surface of the plate. The bone plate system includes a locking system connected to the plate. The locking system is configured to include an unlocked configuration, a first locked configuration and a second locked configuration. In the unlocked configuration, the fastener is removable from the hole in a proximal direction and permitted to angulate with respect to the plate. In the first locked configuration, the fastener is prevented from being removed from the hole in a proximal direction and is permitted to angulate with respect to the plate. In the second locked configuration, the angulation of the fastener with respect to the plate is fixed and the fastener is prevented from being removed from the hole in a proximal direction.

According to another aspect of the invention, a bone plate system is provided. The bone plate system includes a first plate having at least one hole configured to receive a bone fastener. The first plate has a top surface and a bottom surface interconnected by a side surface. The first plate has a distal extension with an aperture extending between the top surface and the bottom surface. The plate system includes a second plate having at least one hole configured to receive a bone fastener. The second plate has a top surface and a bottom surface interconnected by a side surface. The second plate also has a slot at the proximal end sized and configured to receive the distal extension of the first plate. The bone plate system further includes an elongated rack having an outer surface. The elongated rack includes teeth formed on the outer surface. The rack is located between the first plate and the second plate. The bone plate system includes a pinion having a proximal end and a distal end interconnected by an outer surface. The pinion includes teeth formed on the outer surface and a central bore extending between an opening at the proximal end and an opening at the distal end. The pinion is located between the first plate and the second plate. The opening at the proximal end defines a socket configured to receive a driving tool. The bone plate system further includes a pinion pin located inside the central bore of the pinion. The bone plate system further includes a lock located between the first plate and the second plate. The lock includes at least one projection extending toward the teeth of the pinion to arrest rotation of the pinion in either direction. The first plate is connected to the second plate by the rack and pinion such that the first plate is longitudinally movable with respect to the second plate by rotation of the pinion to change the overall longitudinal length of the plate system. Rotation of the pinion in one direction increases the length of the plate system and rotation of the pinion in an opposite direction decreases the length of the plate system. The length of the plate system is always locked by the lock when the pinion is not rotating.

BRIEF DESCRIPTION OF THE DRAWINGS

FIG. 9 is a top planar view of a top plate according to the present invention.

FIG. 10 is a cross-sectional view taken along line 10-10 of FIG. 9 of a top plate according to the present invention.

FIG. 34 is a top perspective view of a fastener lock according to the present invention.

FIG. 35 is a top planar view of an actuator according to the present invention.

FIG. 36 is an end elevational view of an actuator according to the present invention.

FIG. 37 is a side elevational view of an actuator according to the present invention.

DETAILED DESCRIPTION OF THE INVENTION

Figure 1:
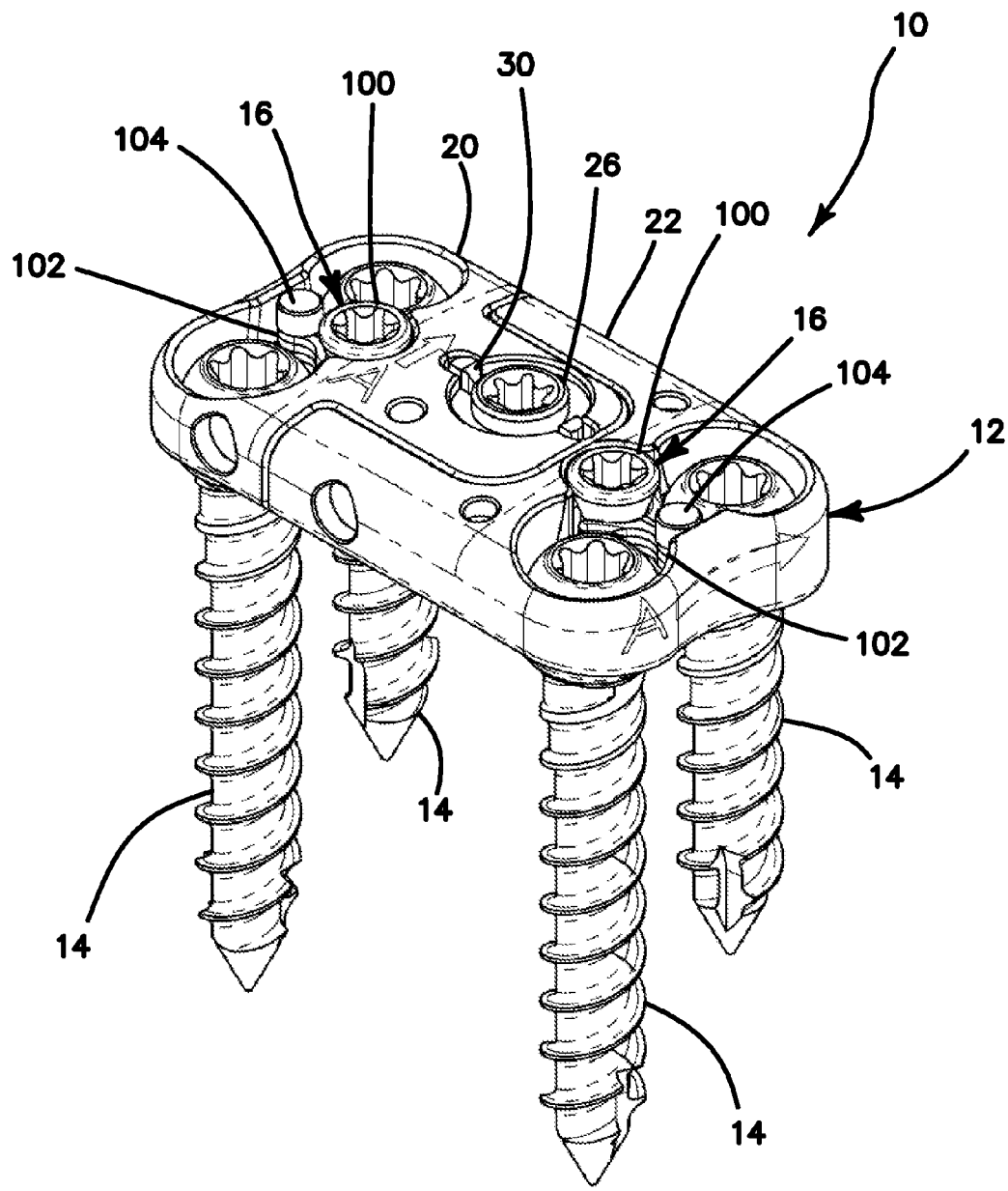
FIG. 1 is a top perspective view of a bone plate system according to the present invention.
Figure 2:
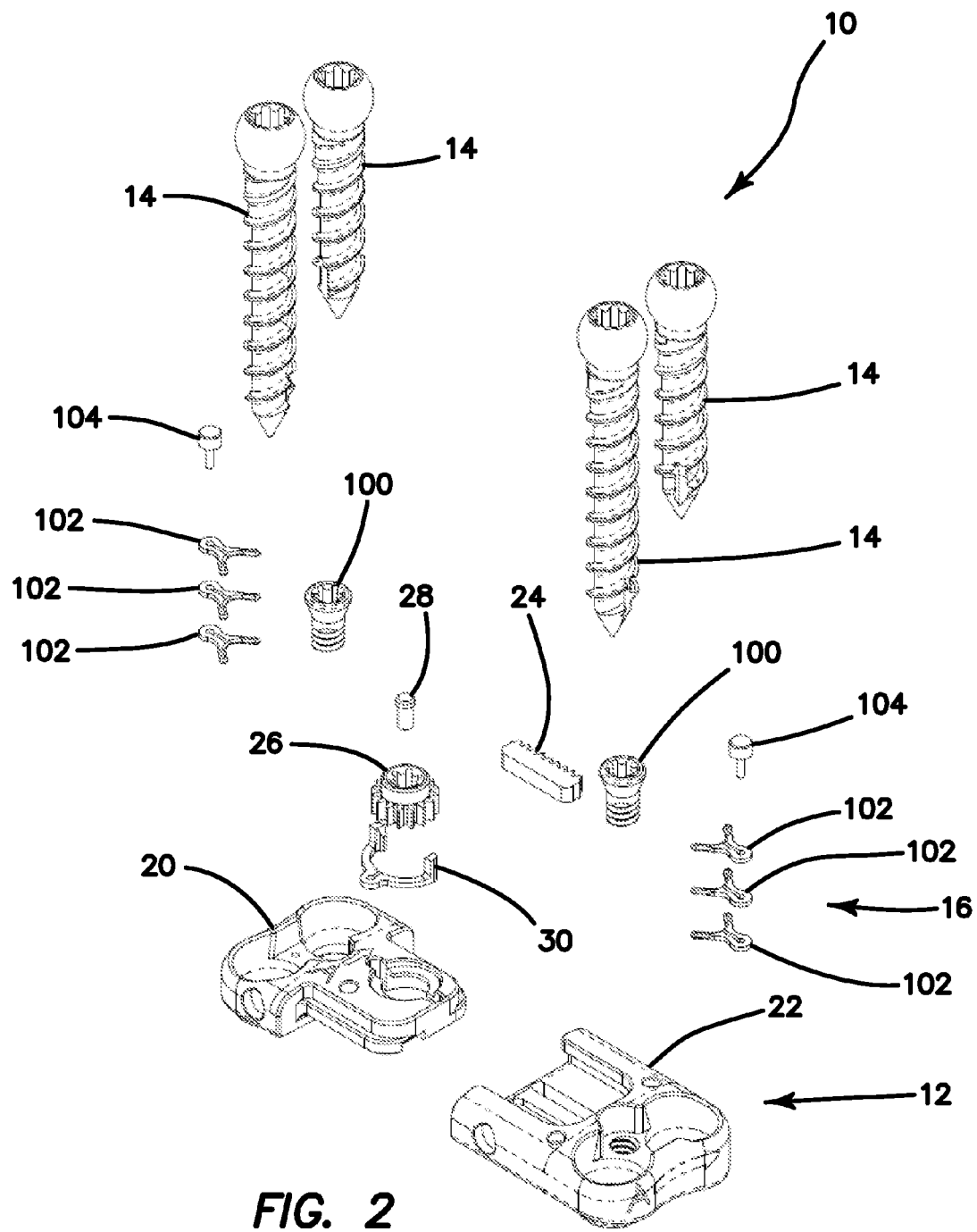
FIG. 2 is a top perspective exploded view of a bone plate system according to the present invention.
Figure 3:
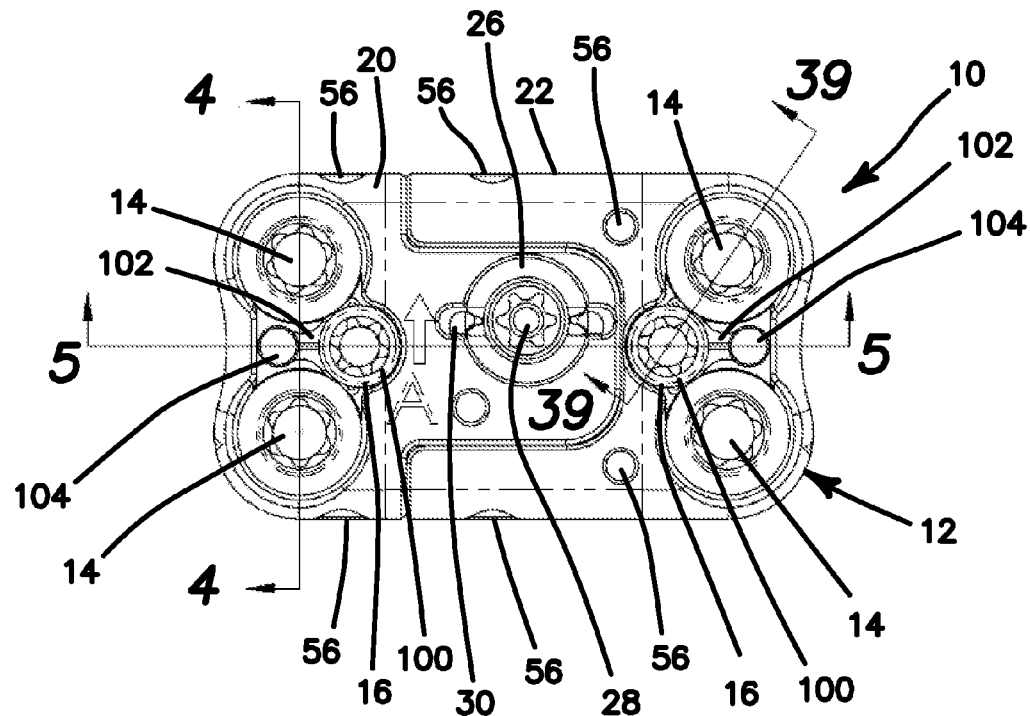
FIG. 3 is a top planar view of a bone plate system according to the present invention.
Figure 4:
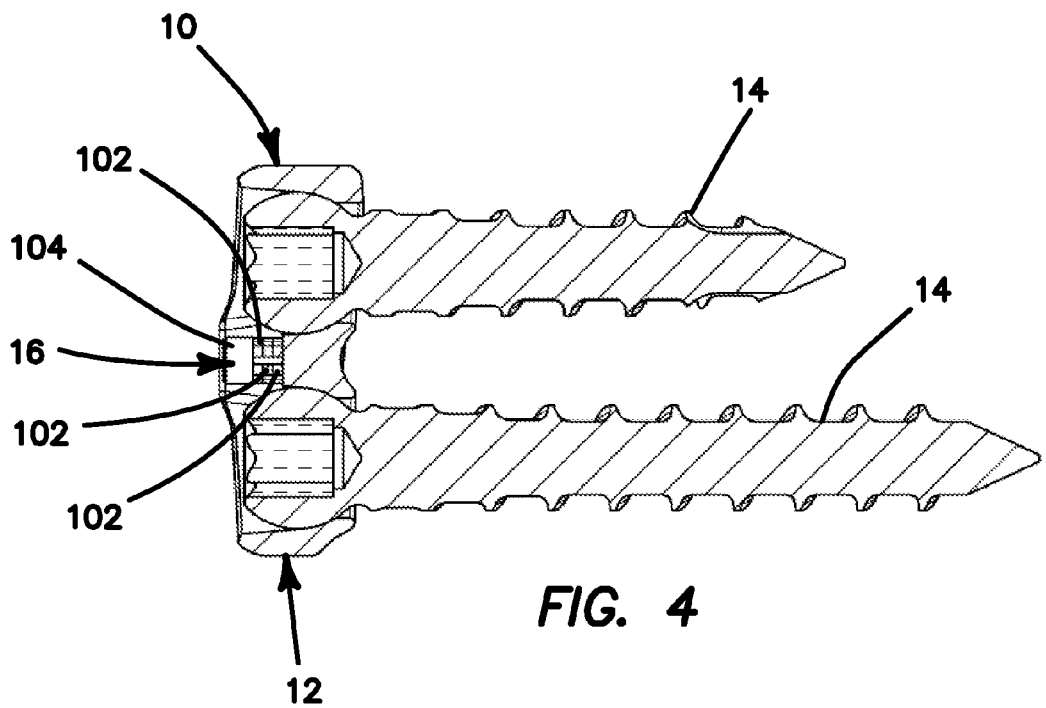
FIG. 4 is a cross-sectional view taken along line 4-4 of FIG. 3 of a bone plate system according to the present invention.
Figure 5:
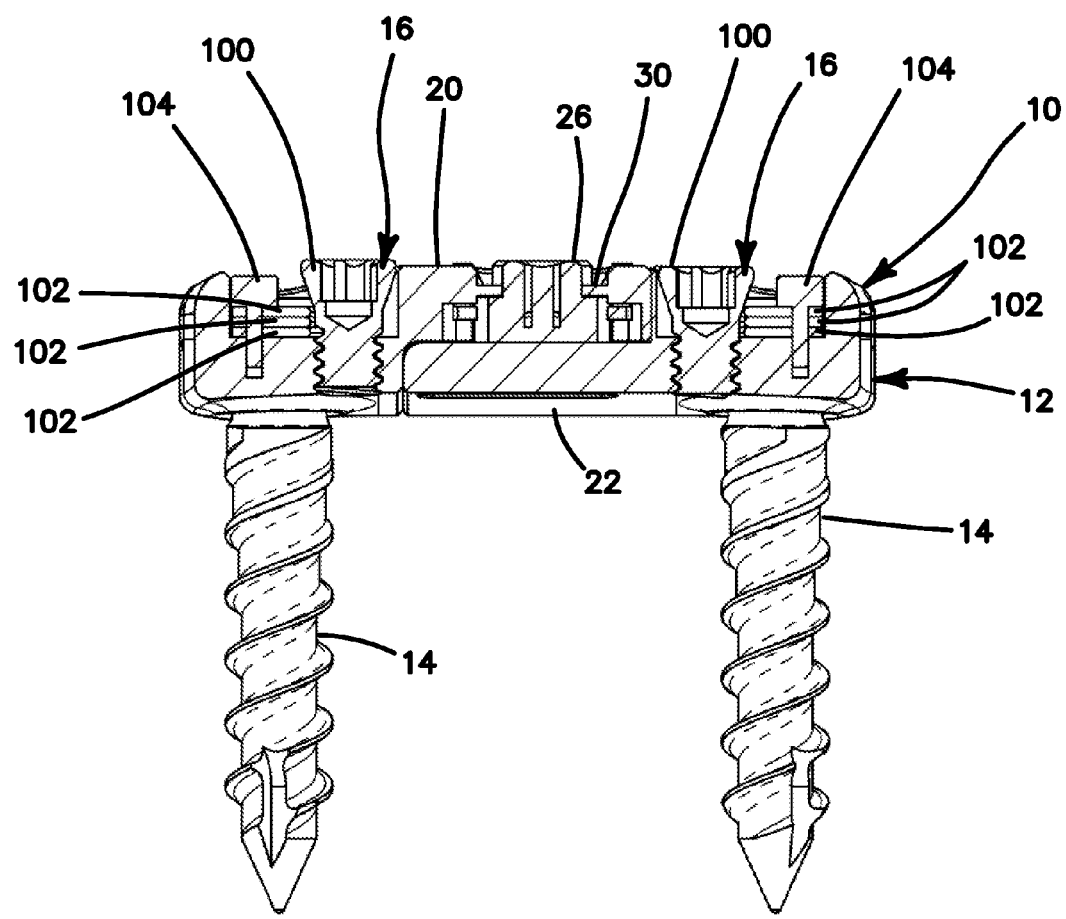
FIG. 5 is a cross-sectional view taken along line 5-5 of FIG. 3 of a bone plate system according to the present invention.
Figure 6:
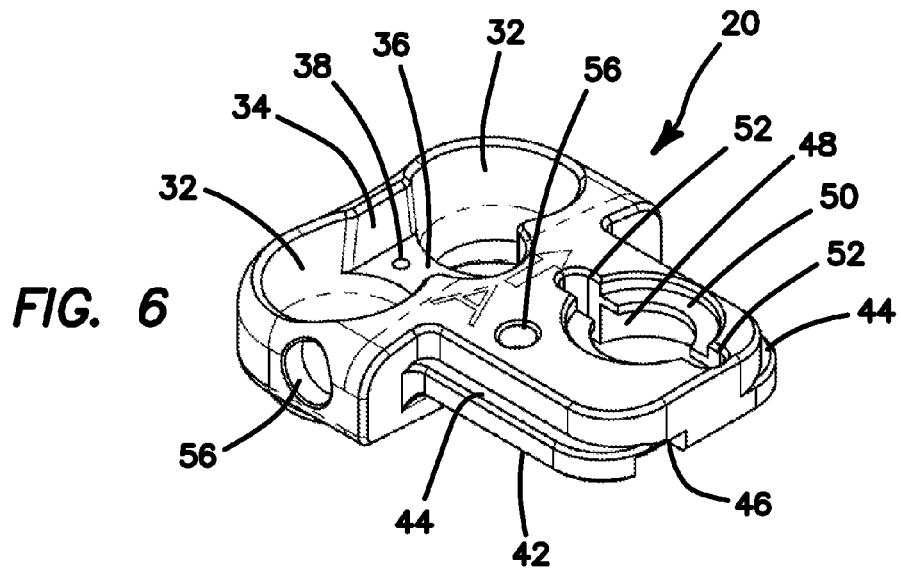
FIG. 6 is a top perspective view of a top plate according to the present invention.
Figure 7:
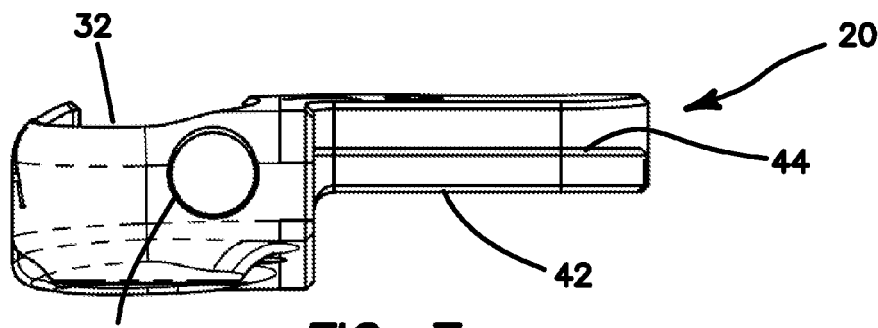
FIG. 7 is a side elevational view of a top plate according to the present invention.
Figure 8:
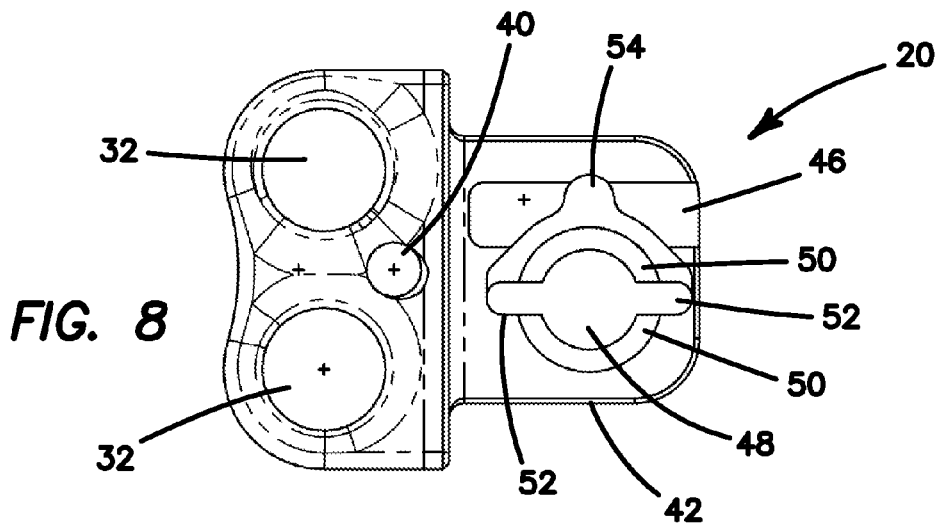
FIG. 8 a bottom planar view of a top plate according to the present invention.
Figure 11:
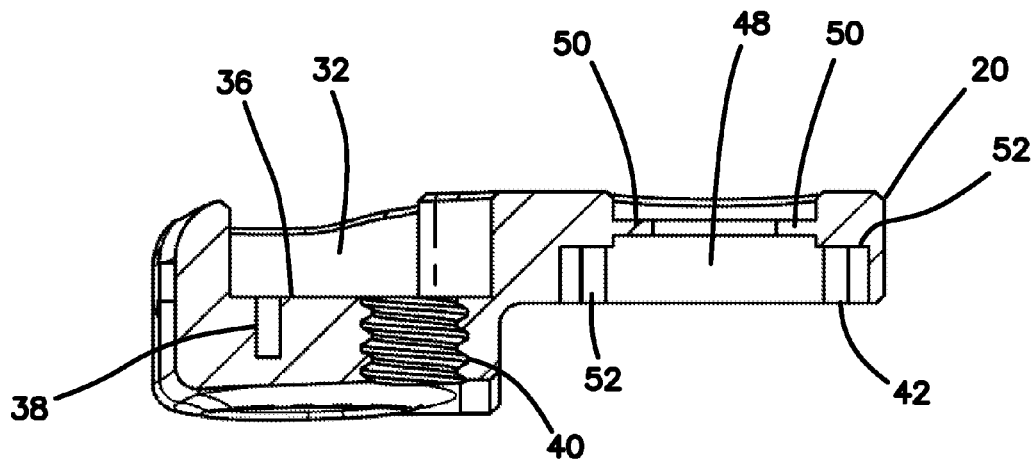
FIG. 11 is a cross-sectional view taken along line 11-11 of FIG. 9 of a top plate according to the present invention.
Figure 12:
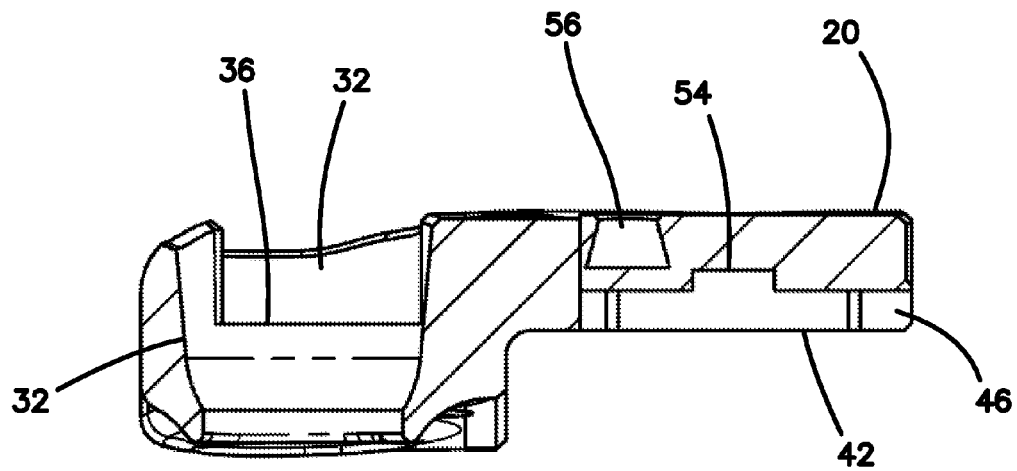
FIG. 12 is a cross-sectional view taken along line 12-12 of FIG. 9 of a top plate according to the present invention.
Figure 13:
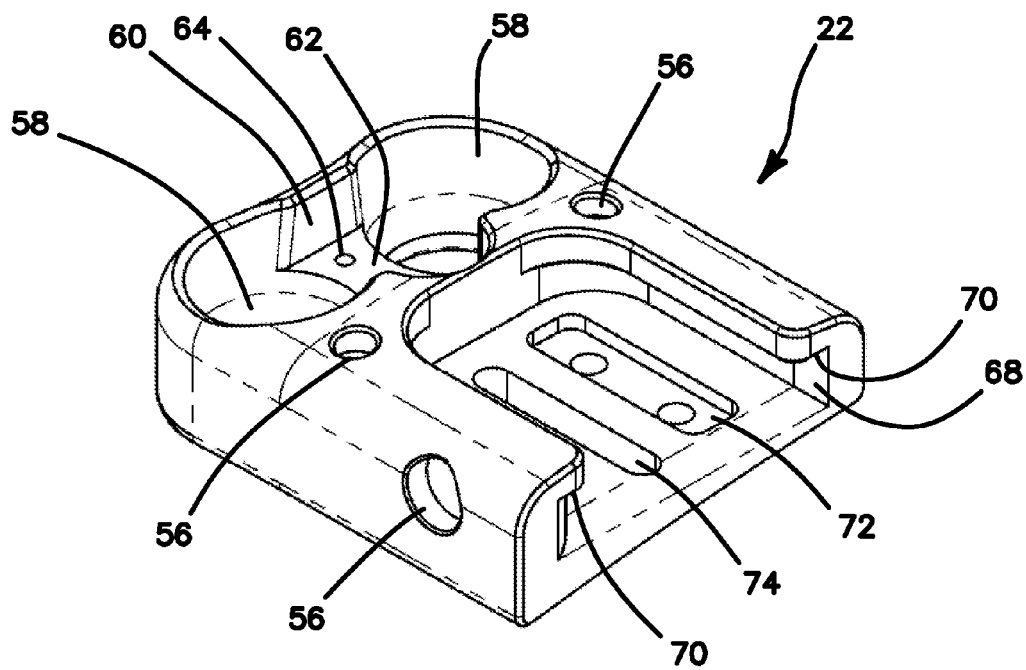
FIG. 13 is a top perspective view of a bottom plate according to the present invention.
Figure 16:
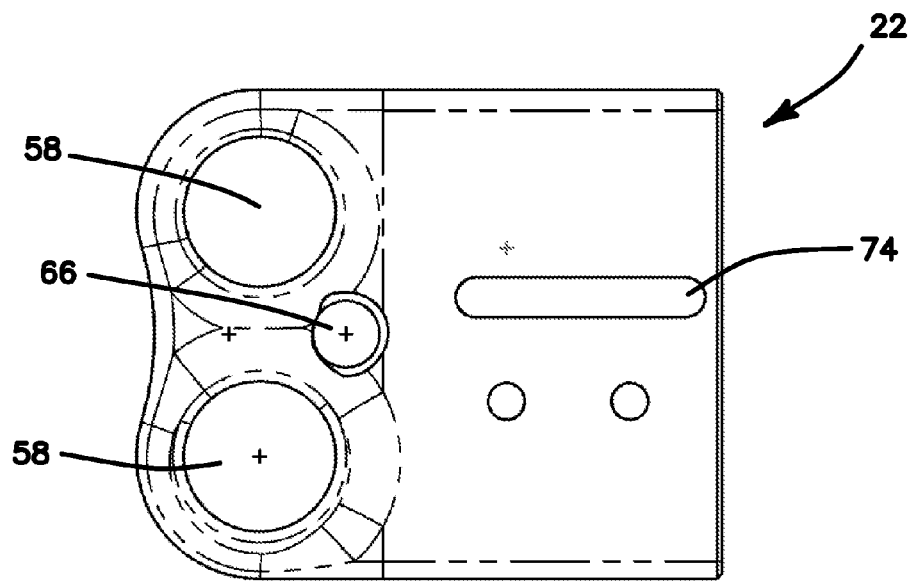
FIG. 16 is a bottom planar view of a bottom plate according to the present invention.
Figure 14:
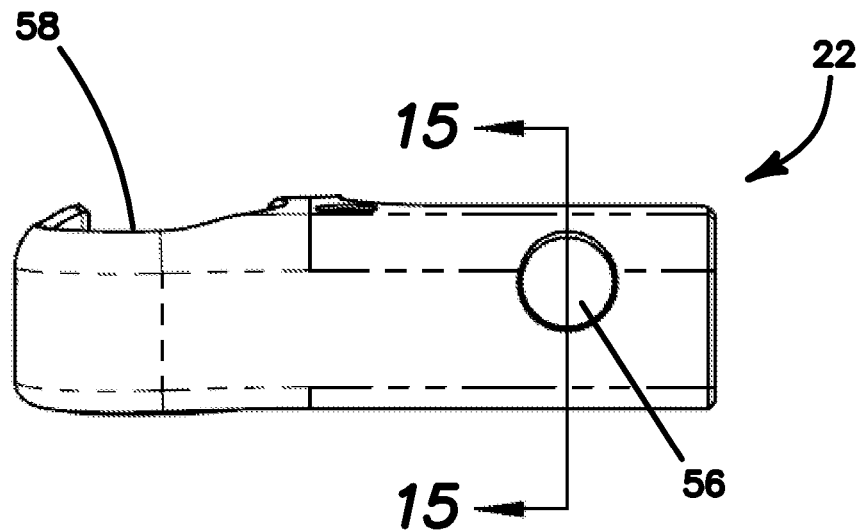
FIG. 14 is a side elevational view of a bottom plate according to the present invention.
Figure 15:
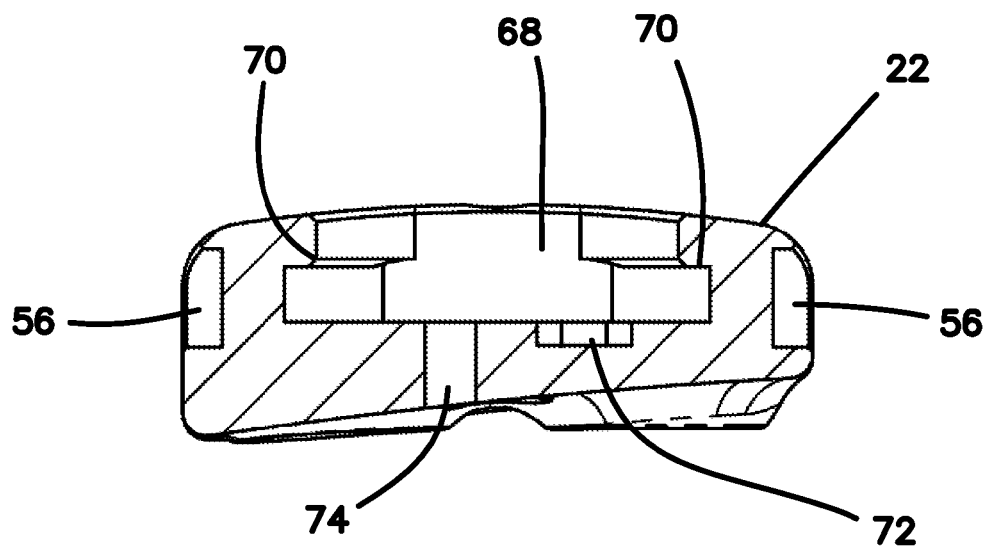
FIG. 15 is a cross-sectional view taken along line 15-15 of FIG. 14 of a bottom plate according to the present invention.
Figure 17:
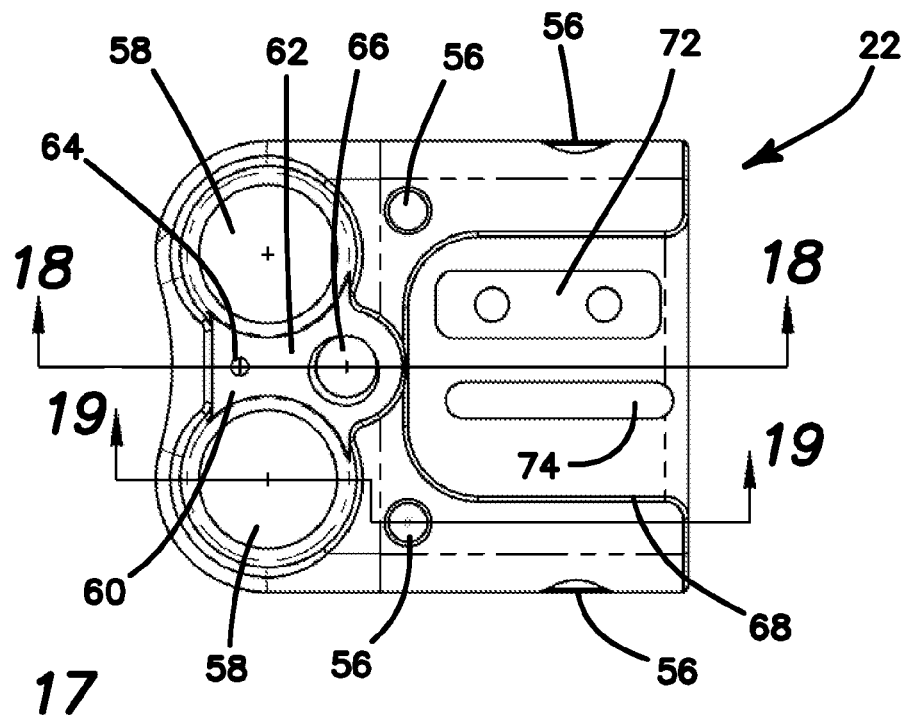
FIG. 17 is a top planar view of a bottom plate according to the present invention.
Figure 18:
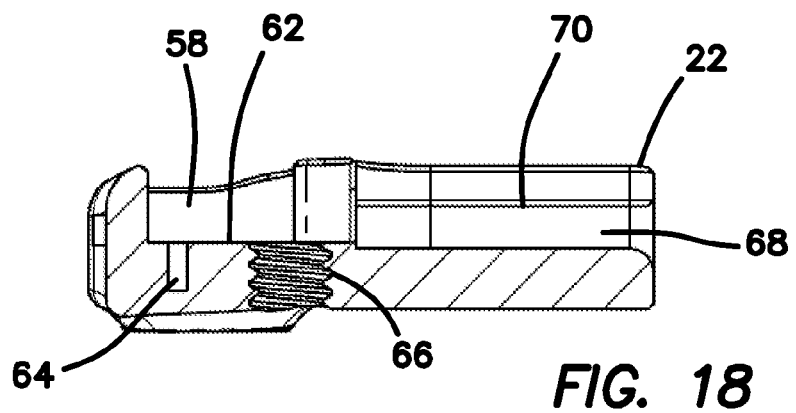
FIG. 18 is a cross-sectional view taken along line 18-18 of FIG. 17 of a bottom plate according to the present invention.
Figure 19:
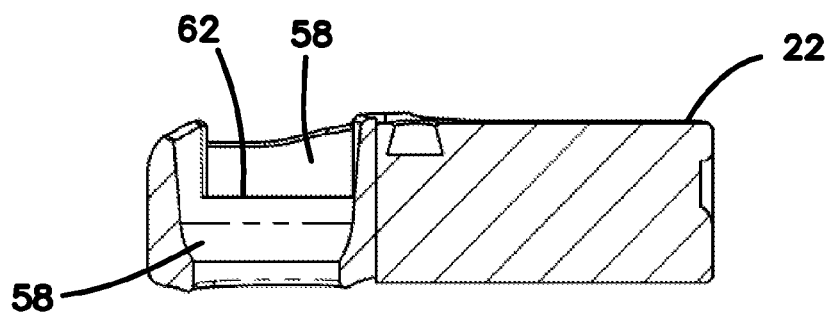
FIG. 19 is a cross-sectional view taken along line 19-19 of FIG. 17 of a bottom plate according to the present invention.

FIGS. 1-5 depict a bone plate system 10 according to one variation of the invention that may be used to stabilize or fuse vertebral bodies of the spine to allow fusion by holding the vertebral bodies in proper alignment, and thus allowing the spine to heal. The bone plate system 10 that is shown in FIGS. 1-5 is a single-level bone fixation plate that is configured to span across a single disc and fixate two vertebrae of the spine although the bone plate system 10 may be a two-level or any multilevel bone plate spanning two or more vertebral bodies. The bone plate system 10 is attachable to the lateral aspect of the two or more vertebrae; however, the invention is not so limited and the plate can be employed in anterior, posterior, antero-lateral or oblique positions with respect to two or more vertebrae. The plate can be employed for spinal stabilization in conjunction with anterior or posterior fusion procedures for placement of the fusion construct in a disc space between vertebrae. The bone plate system 10 can be attached to any one or combination of the cervical, thoracic, lumbar and sacral regions of the spinal column as well as be employed in other skeletal fixations. The plate 10 can be employed unilaterally, in which a single plate is attached to the vertebrae along one side of the midline of the spinal column. The plate system 10 can also be employed bi-laterally in which two plates 10 are attached to the vertebrae on opposite sides of the midline of the spinal column. The bone plate system 10 comprises a plate 12 and fasteners 14 retained by one or more lock system 16. The fasteners 14 are inserted through the plate 12 to attach the plate 12 to bone. The plate system 10 shown in FIGS. 1-5 is an expandable plate; however, the invention is not so limited. With the fasteners 14 inserted into the plate 12, the at least one lock system 14 is employed to provide anti-back out protection for the fasteners 14.

Turning now to FIGS. 6-19, the plate 12 will now be described in greater detail. The plate 12 is an expandable plate assembly comprising a top plate 20 interconnected with a bottom plate 22 such that the top plate 20 is movable relative to the bottom plate 22. The top plate 20 is interconnected with the bottom plate 22 with a rack 24 configured to engage a pinion 26 that is secured to the plate 12 with a pinion pin 28. A pinion lock 30 is provided to lock the rotation of the pinion 26 relative to the plate 12 and, hence, also lock the position of the top plate 20 relative to the bottom plate 22. The top plate 20 is positionable along an upper vertebra and the bottom plate 22 is positionable along a lower vertebra, or vice versa, and a middle portion therebetween extending along the spinal disc space between the adjacent vertebrae.

The plate 12 and other components of the bone plate system 10 are made from suitable biocompatible material such as stainless steel, titanium and or any other metal or metal alloy. One or more components may be made of non-metal materials including but not limited to polymer, carbon reinforced polyetheretherketone (PEEK) or one or more biocompatible ceramics. The plate 12 may be additionally configured to promote bone ingrowth to the plate 12 such as a portion of the plate 12 being made of porous material or being roughened by mechanical blasting or plasma spraying with metal particles of one or more sizes. The plate 12 may also be coated with bio-active material, therapeutic agents for enhancing bone fusion and ingrowth, bone morphogenic proteins, growth factors and the like.

With reference to FIGS. 6-12, the top plate 20 will now be described. The top plate 20 includes an upper surface and a lower surface. The upper surface and lower surface are interconnected by curved side walls and end walls to form a generally rectangular shape that is substantially symmetrical about a midline. The plate 12 is gently curved to complement the natural curved structure of the vertebral bodies. The corners of the plate 12 are rounded to reduce impingement on the surrounding tissue. The plate 12 can be fixed to each vertebra by at least one bone-engaging fastener 14 adjacent each end of the plate 12. In the variation shown in the figures, the top plate 20 includes a pair of holes 32 for receiving bone-engaging fasteners 14 to engage the plate 12 to an upper vertebra. Each hole 32 extends between the top surface and the bottom surface of the top plate 20. The pair of holes 32 is adjacent to a lock-receiving location 23. The lock-receiving location 34 is formed between the pair of holes 32 in the top plate 20. The lock-receiving location 34 is configured to receive the lock system 16 that provides anti-back out protection for the fasteners 14. The lock-receiving location 34 is a recess in the top plate 20 that extends downwardly from the top surface to a base surface 36. In the base surface 36, a pin aperture 38 and an actuator aperture 40 are formed. The pin aperture 38 and actuator aperture 40 are clearly seen in FIG. 11 extending downwardly from the base surface 36. The actuator aperture 40 is shown to include a threaded inner surface for engaging with a threaded outer surface of the actuator 100 of the lock system 16 to connect the actuator 100 of the lock system 16 to the top plate 20. The pin aperture 38 is sized and configured for receiving a pin 104 of the lock system 16 for connecting bone screw locks 102 of the lock system 16 to the top plate 20. At the distal end of the top plate 20 opposite from the pair of bone fastener receiving holes 32, the top plate 20 forms an extension 42 along the top surface as can be seen in the side view of FIG. 7. The extension 42 is sized and configured for sliding into and interconnecting with a complimentary-shaped slot 68 formed in the bottom plate 22. The extension 42 includes a lip 44 along the sides of the extension 42 for engaging an undercut 70 formed in the slot 68 of the bottom plate 22. The extension 42 includes a rack channel 46 sized and configured to receive the rack 24. The rack channel 46 extends longitudinally along the top plate 20. The extension 42 further includes a pinion aperture 48 sized and configured for receiving the pinion 26. The pinion aperture 48 includes a ledge 50 around at least a portion of the inner circumference and extending inwardly toward the center of the pinion aperture 48. Also, the pinion aperture 48 includes oppositely disposed outwardly extending notches 52 sized and configured to receive at least a portion of the pinion lock 30. Furthermore, the extension 42 includes a recess 54 sized and configured to receive the pinion lock 30. The pinion lock receiving recess 54 is clearly visible in FIG. 8. The recess 54 is formed in the bottom surface of the extension 42 and is shaped to conform to the shape of the pinion lock 30. The depth of the recess 54 serves to retain the pinion lock 30 in position relative to the top plate 20. The top plate 20 also includes a plurality of holes 56 for engaging instruments configured to grab the plate 12. The holes 56 are formed in the top and/or side surfaces of the top plate 20 and extend inwardly therefrom. The holes 56 provide ways to grab the plate 12 from the top or from the sides or for attachment to and purchase with various tools including tools for moving the top plate 20 relative to the bottom plate 22.

Turning now to FIGS. 13-19, the bottom plate 22 will now be described. The bottom plate 22 includes an upper surface and a lower surface. The upper surface and lower surface are interconnected by curved side walls and end walls to form a generally rectangular shape. The bottom plate 22 includes a pair of holes 58 for receiving bone-engaging fasteners 14 to engage the plate 12 to a lower vertebra. Each hole 58 extends between the top surface and the bottom surface of the bottom plate 22. The holes 58 are adjacent to each other. At a location between the two holes 58, a lock-receiving location 60 is formed in the bottom plate 22. The lock-receiving location 60 is configured to receive the lock system 16 that resists bone fasteners 14 from backing out of the plate 12 in situ. The lock-receiving location 34 is a recess in the bottom plate 22 that extends downwardly from the top surface to a base surface 62, which forms the floor of the recess. The base surface 62 includes a pin aperture 64 that extends downwardly from the base surface 62. The pin aperture 64 is sized and configured for receiving a pin 104 of the lock system 16 for connecting the fastener locks 102 of the lock system 16 to the bottom plate 22. The base surface 62 also includes an actuator aperture 66 that extends downwardly from the base surface 62. The actuator aperture 66 is clearly shown in FIG. 18 to include a threaded outer inner surface and configured for engaging with a threaded outer surface of the actuator 100 of the lock system 16 to connect the actuator 100 of the lock system 16 to the bottom plate 22. The bottom plate 22 includes a slot 68 that opens to the top surface and has an entrance opening at the proximal end of the bottom plate 22. The slot 68 is a recess that extends downwardly from the top surface of the bottom plate 22 and opens at the proximal end. The slot 68 includes an undercut 70 seen in FIGS. 13, 15 and 18. The slot 68 is sized and configured to receive at least a portion of the top plate 20. The undercut 70 is configured to engage the lip 44 of the top plate 20 when the extension 42 of the top plate 20 is inserted into the slot 68 of the bottom plate 22 to retain the top plate 20 relative to the bottom plate 22. The extension 42 and slot 68 are configured such that top plate 20 can translate in the longitudinal direction relative to the bottom plate 22 and is constrained from moving laterally by the side walls of the slot 68 and also constrained by the undercut 70 from moving along a z-axis. Hence, the top plate 20 is configured to slide with respect to the bottom plate 22. When inserted into the slot 68, the top surface of the top plate 20 is flush with the top surface of the bottom plate 22. The top plate 20 is inserted into the slot 68 of the bottom plate 22 through the open proximal end of the bottom plate 22. The bottom plate 22 further includes a rack channel 72 seen in FIGS. 13, 15 and 17. The rack channel 72 is a recess located inside the slot 68. The rack channel 72 extends downwardly from the bottom surface of the slot 68 and is sized and configured to receive the rack 24. Alternatively, the rack 24 may be integrally formed with the bottom plate 22. The rack channel 72 of the bottom plate 22 and the rack channel 46 of the top plate 20 retain the rack 24 in position. The bottom plate 22 further includes a long narrow opening 74 in the location of the slot 68. The opening 74 extends from the bottom surface of the slot 68 all the way through to the bottom surface of the bottom plate 22. The opening 74 is sized and configured for receiving the pinion pin 28 such that the pinion pin 28 translates along the length of the opening 74 when the top plate 20 is moved relative to the bottom plate 22. The ends of the opening 74 serve as stop against which the pinion pin 28 abuts to prevent separation of the top plate 20 from the bottom plate 22. The bottom plate 22 also includes a plurality of holes 56 that extend inwardly from the top surface and/or side surface of the bottom plate 22. The holes 56 provide a number of ways to grab or attach to the plate 12 with various tools.

Figure 20:
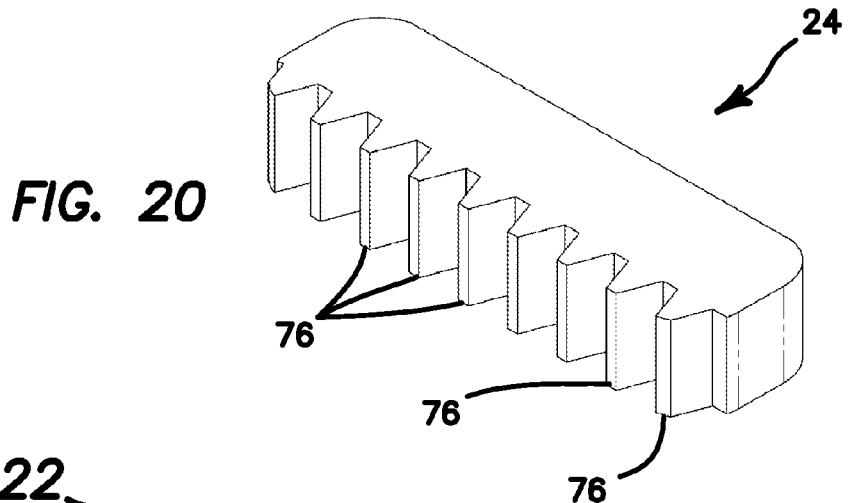
FIG. 20 is a top perspective view of rack according to the present invention.

Turning now to FIG. 20, there is shown a rack 24 according to the present invention. The rack 24 is an elongate element substantially rectangular in shape having a top surface and bottom surface interconnected by side surfaces and end surfaces. One of the side surfaces includes a plurality of teeth 76 extending between the top surface and the bottom surface. The teeth 76 are configured to engage teeth on the pinion 26.

Figure 21:
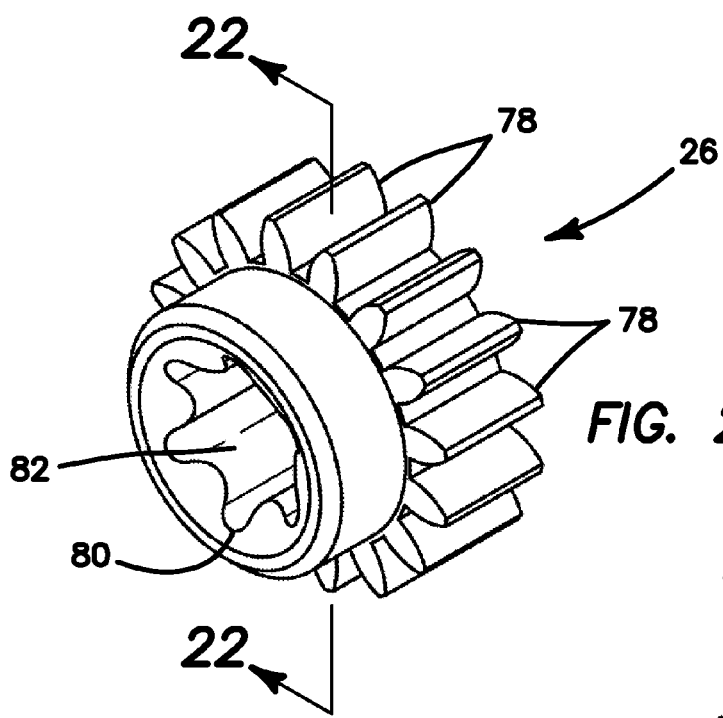
FIG. 21 is a top perspective view of pinion according to the present invention.
Figure 22:
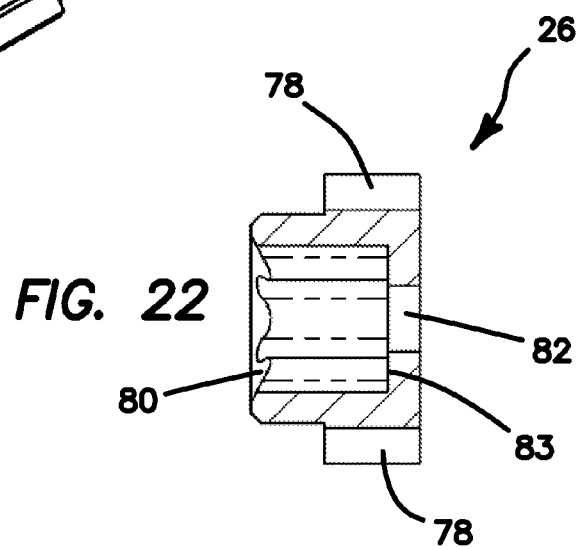
FIG. 22 is a cross-sectional view taken along line 22-22 of FIG. 21 of a pinion according to the present invention.
Figure 23:
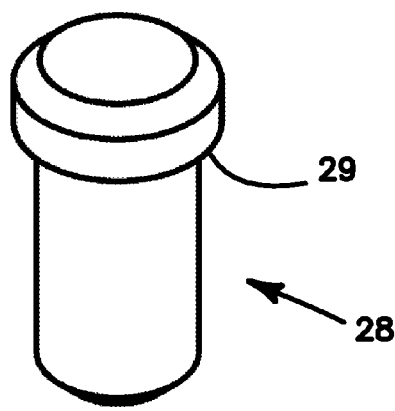
FIG. 23 is a top perspective view of a pinion pin according to the present invention.

Turning now to FIGS. 21-22, there is shown a pinion 26 according to the present invention. The pinion 26 is substantially cylindrical in shape having a proximal end and a distal end. The outer surface of the pinion 26 includes a plurality of teeth 78 extending outwardly from the outer surface and formed around the perimeter of pinion 26. The proximal end of the teeth 78 begins at a distance distal to the proximal end of the pinion 26 and the teeth 78 extend longitudinally to the distal end of the pinion 26. Hence, there is a portion of the pinion 26 near the proximal end without teeth that defines a smooth outer surface. The pinion 26 includes a central bore 82 that extends axially between an opening at the proximal end and an opening at the distal end of the pinion 26. The central bore 82 includes an inner circumferential ledge 83 from which the central bore 82 extends with a reduced diameter to the distal end of the pinion 26. The central bore 82 is sized and configured to receive a cylindrical pinion pin 28. The pinion pin 28 is illustrated in FIG. 23. The pinion pin 28 includes a circumferential ledge 29 that defines the intersection of a larger head portion from a narrower shank portion. The circumferential ledge 29 of the pinion pin 28 engages with the circumferential ledge 83 of the central bore 82 of the pinion 26 when the pinion pin 28 is inserted into the central bore 82. The opening at the proximal end of the pinion defines a socket 80 that is configured to engage a driving tool. The socket 80 forms an instrument recess that is shaped for receiving a complementary-shaped tip of a surgical driving tool. A substantially hexagonal, daisy-shaped recess is shown in FIG. 21; however, the socket can be of any shape that allows a surgical tool to drive the pinion 26. The pinion pin 28 is insertable into the central bore 82 such that the proximal end of the pinion pin 28 is distal to the proximal end of the pinion 26 so as to not to interfere with the insertion of a driving tool into the socket 80 at the proximal end. However, the pinion pin 28 is long enough to extend out from the opening of the central bore 82 at the distal end of the pinion 26. The portion of the pinion pin 28 that is distal to the distal end of the pinion 26 resides within the narrow opening 74 of the bottom plate 22 within which the pinion pin 26 may translate. The portion of the pinion pin 28 that is distal to the distal end of the pinion 26 serves as stop against the ends of the narrow opening 74.

Figure 24:
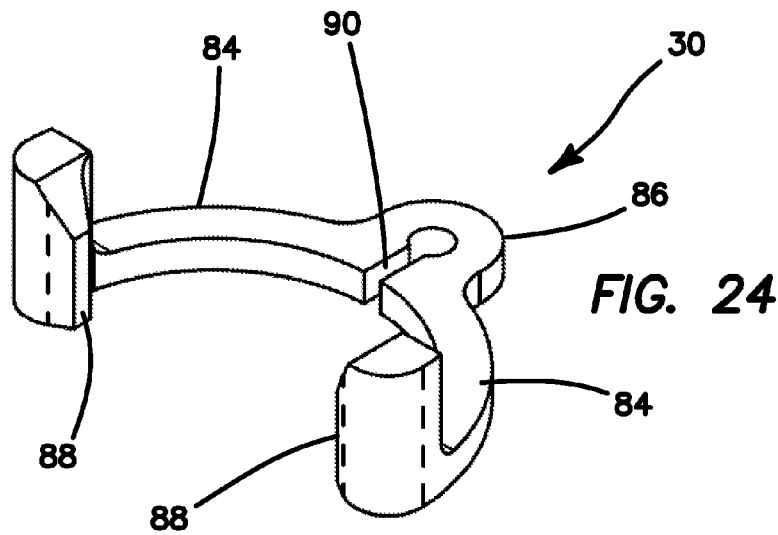
FIG. 24 is a top perspective view of a pinion lock according to the present invention.
Figure 25:
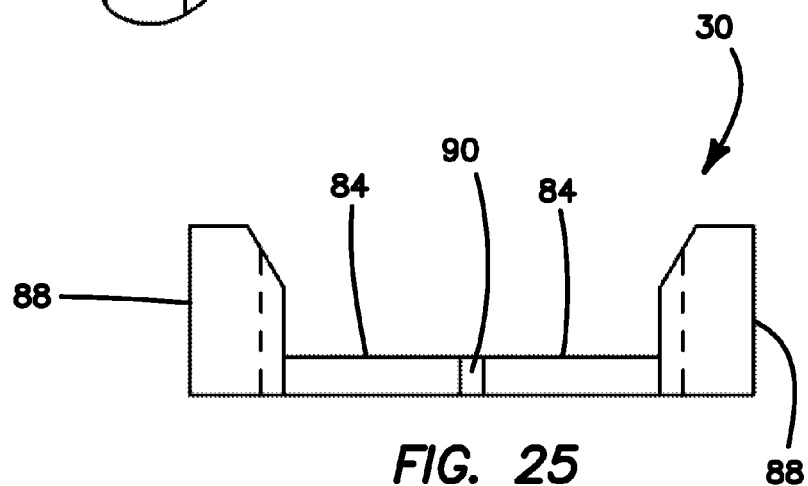
FIG. 25 is an end elevational view of a pinion lock according to the present invention.
Figure 26:
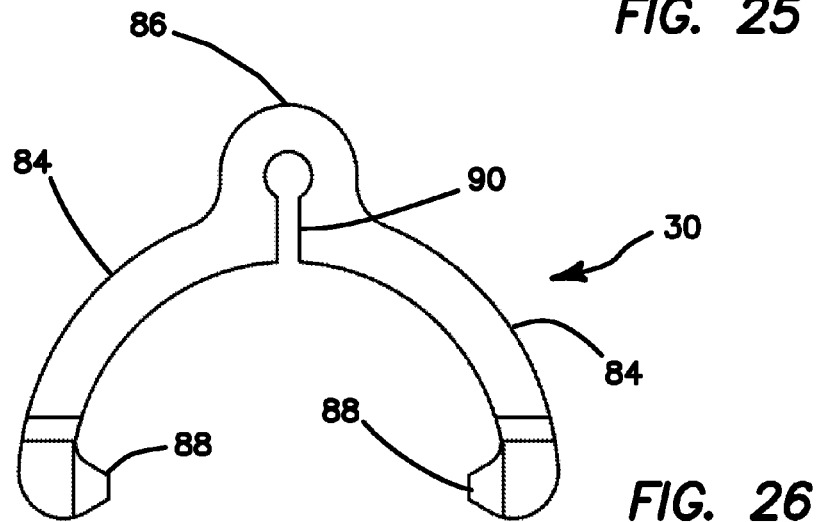
FIG. 26 is a top planar view of a pinion lock according to the present invention.
Figure 28:
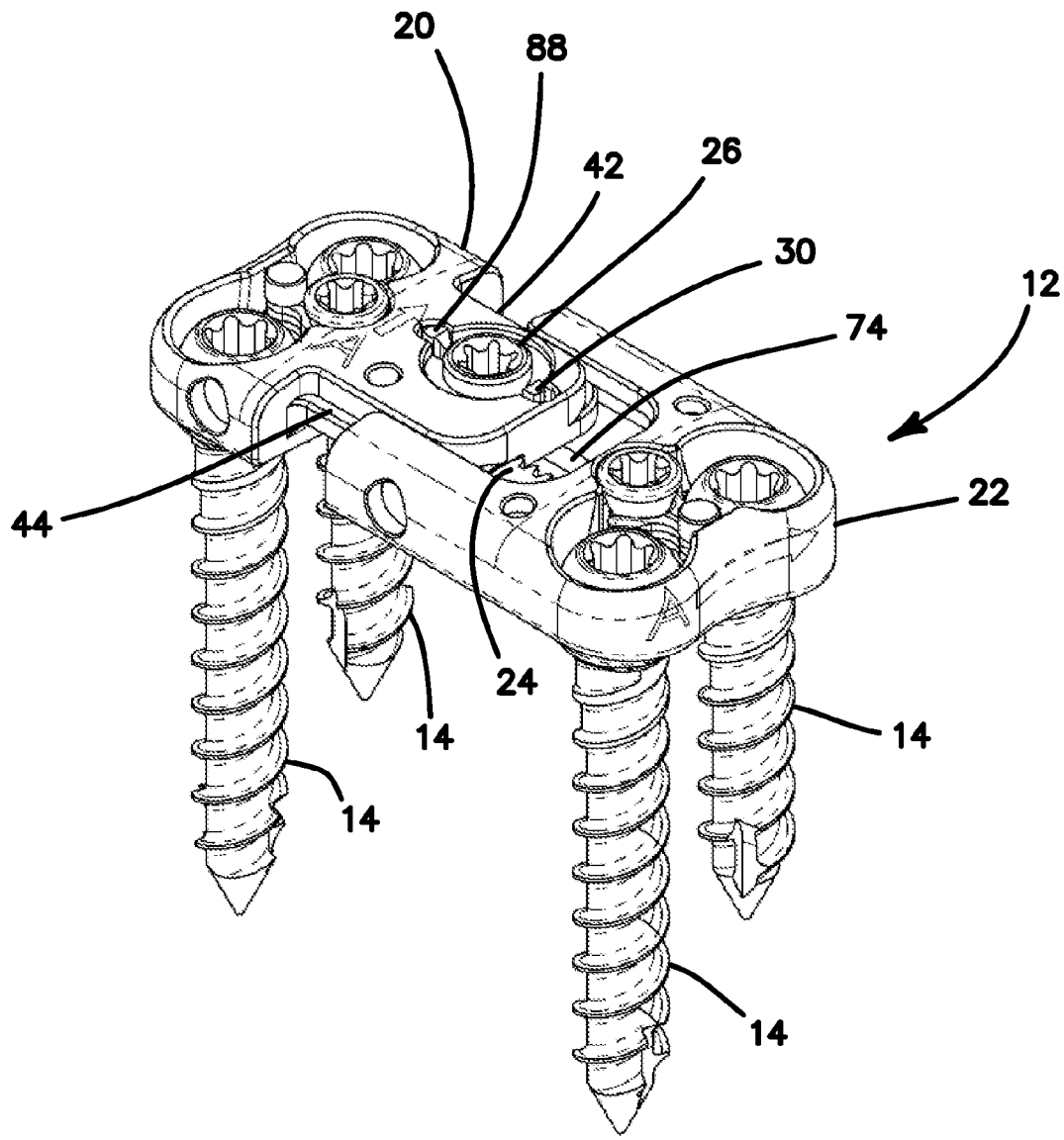
FIG. 28 is a top perspective view of a bone plate system in an expanded configuration according to the present invention.
Figure 29:
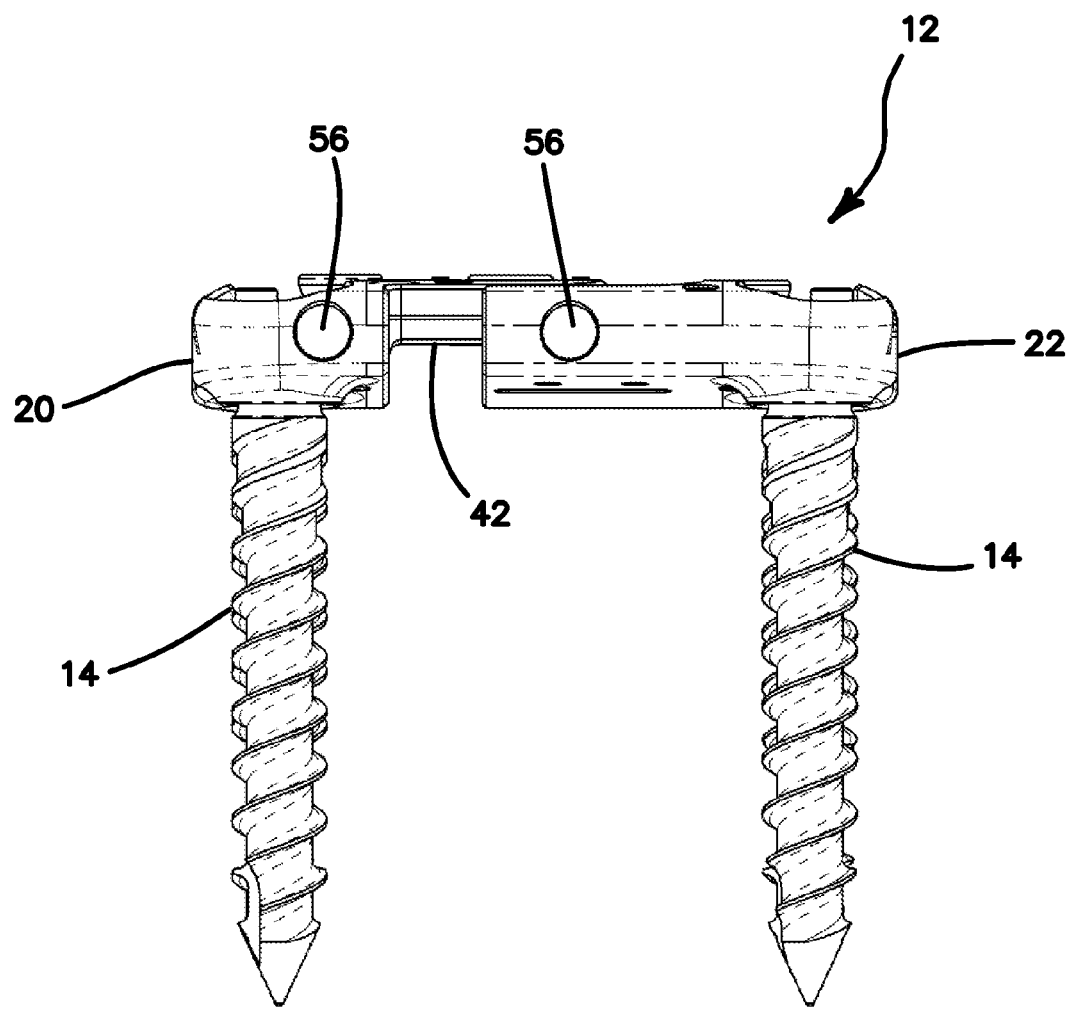
FIG. 29 is a side elevational view of a bone plate system in an expanded configuration according to the present invention.
Figure 30:
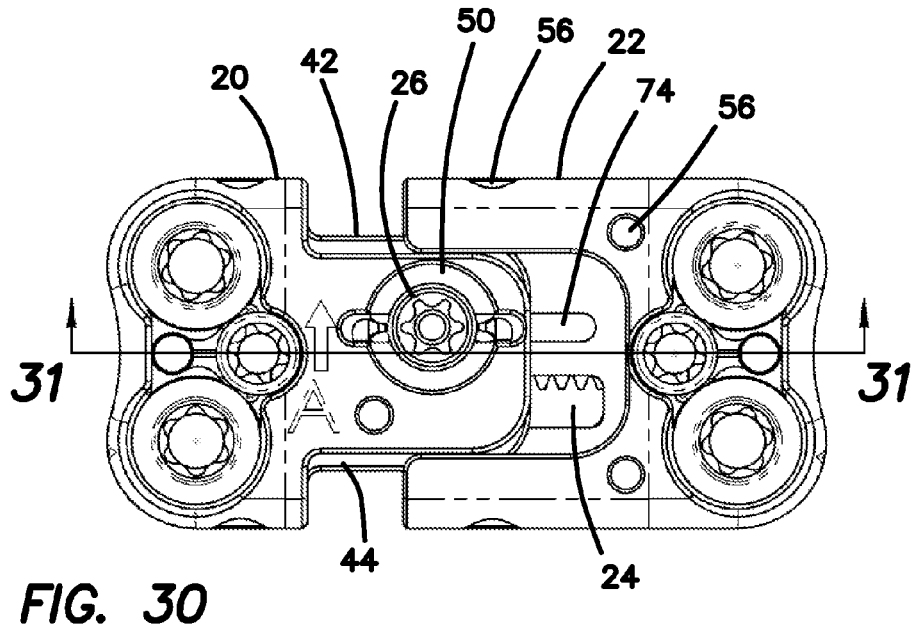
FIG. 30 is a top planar view of a bone plate system in an expanded configuration according to the present invention.
Figure 31:
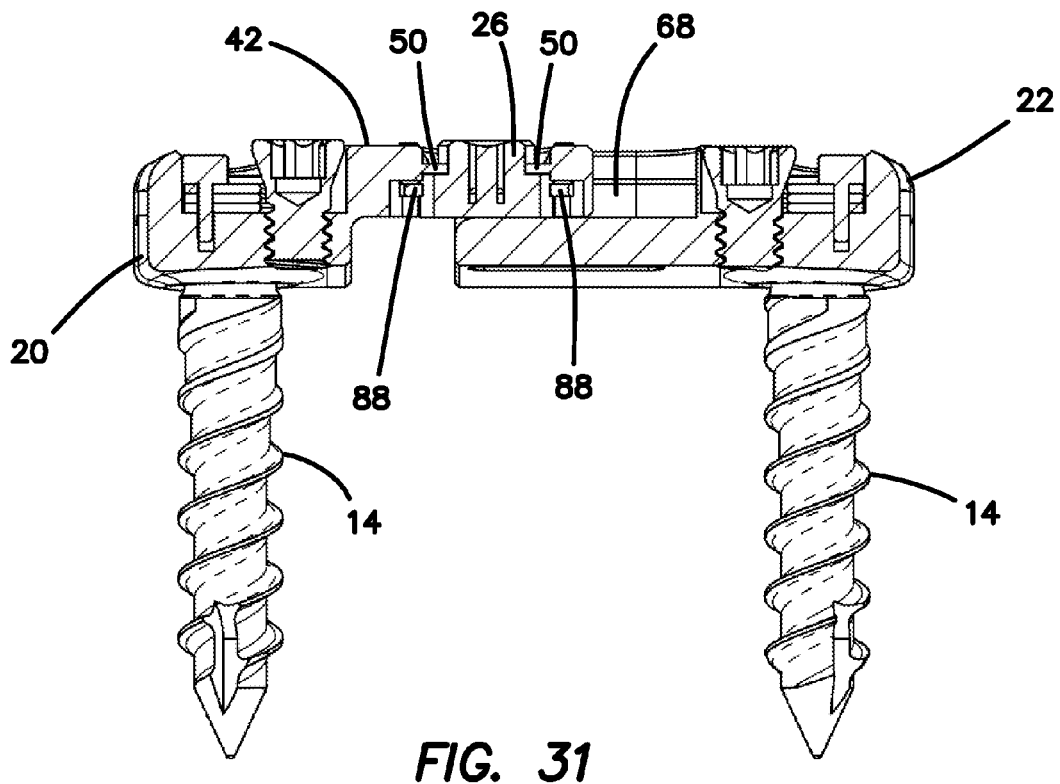
FIG. 31 is a cross-sectional view taken along line 31-31 of FIG. 30 of a bone plate system in an expanded configuration according to the present invention.

Turning now to FIGS. 24-26, the pinion lock 30 will now be described. The pinion lock 30 is wishbone-shaped or substantially "Y" shaped having two bowed or curved arms 84 that interconnect at a proximal end 86. The two arms 84 of the Y-shaped pinion lock 30 lie substantially in one plane defining a thickness between a top surface and a bottom surface. At least one cog-like projection 88 is formed at the distal end of each arm 84. The projection 88 extends upwardly from the top surface of the pinion lock 30. Also, the projection 88 extends inwardly towards the midline of the pinion lock 30. The projections 88 are configured to engage between the teeth 78 of the pinion 26 and configured to arrest the rotation of the pinion 26 relative to the plate 12.

The arms 84 bow around at least a portion of the pinion 26 and the projections 88 are oppositely disposed from each other to engage the pinion 26 from opposite directions. Along the midline of the pinion lock 30 at the proximal end 86 a slot 90 is formed. The slot 90 is located between the arms 84 and includes an open distal end. The proximal end of the slot 90 terminates at a circular end. The slot 90 provides the pinion lock 30 with added resiliency such that when the arms 84 are flexed outwardly from their natural state under force of a rotating pinion 26, the arms 84 spring back inwardly toward the midline about a fulcrum near the proximal end 86 and return to their natural state. Such outward flexing of the arms 84 occurs when the pinion 26 is rotated and the teeth 78 on the pinion 26 engage the projections 88 of the pinion lock 30 pushing the arms 84 outwardly from which the arms 84 spring back inwardly to interlock between the teeth 78 of the pinion 26 again.

Figure 27:
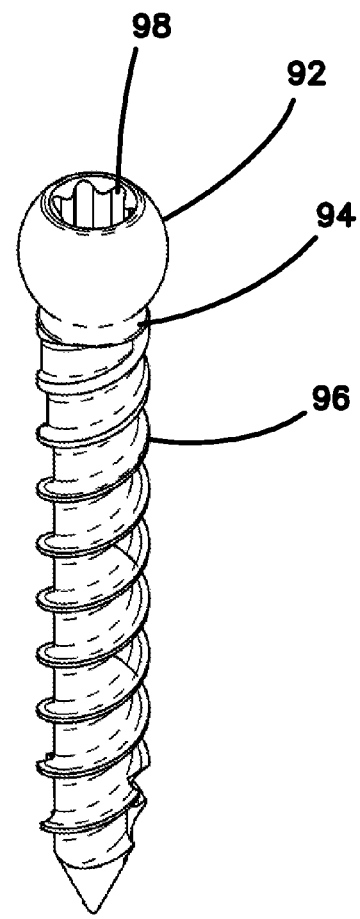
FIG. 27 is a top perspective view of a bone fastener according to the present invention.

With particular reference to FIG. 27, an exemplary orthopedic fastener 14 that is preferably used with the bone plate system 10 of the present invention is a bone screw 14. The bone screw 14 includes a screw head 92, neck 94 and threaded shank 96. The head 92 is bulbous having a larger lateral dimension than the threaded shank 96. Also, the outer surface of the head 92 is curved, spherical in shape or partially spherical or a frustum or frusta of a sphere having a region of a sphere delimited by one plane parallel to a plane containing a diameter or having a region of a sphere delimited by two planes which in one variation may be parallel to each other. The proximal plane of the frusta-spherical head 92 includes an opening that serves as an instrument recess or socket 98 configured to engage a complementary tip of a surgical tool for driving the bone screw into bone. A substantially hexagonal, daisy-shaped recess 98 is shown in FIG. 27; however, the recess 98 can be of any shape that allows a surgical tool to drive the bone screws 14 into the vertebral column. The head 92 of the bone screw 14 corresponds to the shape of the holes 32, 58 in the top plate 20 and bottom plate 22, respectively. Alternatively, the holes 32, 58 may be provided with a retention ring with a conforming surface to prevent the fastener 14 from translating distally through the plate 12. Various bone screws 14 may be employed including ones capable of polyaxial, variable angle or fixed angled orientation with respect to the plate 12 with or without the ability to be locked down at a desired angle or orientation with respect to the plate 12. The present invention does provide for variable angulation of each fastener 14 with respect to the plate 12 and the ability to lock each fastener 14 relative to the plate 12 at a desired angle. The bone screws 14 are preferably self-tapping, however, other screws requiring holes to be drilled or pre-tapped can also be employed.

The plate 12 is assembled by placing the rack 24 inside the rack channel 72 of the bottom plate 22. The bottom surface of the top plate 20 is approached and the pinion lock 30 is placed into the pinion lock 30 receiving location 54 of the top plate 20. The upstanding projections 88 of the pinion lock 30 are located inside the notches 52. The arms 84 of the pinion lock 30 are allowed to flex outwardly within the pinion lock receiving location 54. The bottom surface of the top plate 20 is approached and the pinion 26 is placed into the pinion aperture 48 between the arms 84 of the pinion lock 30 such that the projections 88 of pinion lock 30 are located between the teeth 78 on the pinion 26. The proximal end of the teeth 78 on the pinion 26 abut the ledge 50 in the pinion aperture 48 preventing the pinion 26 from falling out from the top surface of the plate 12. The rack 24 in the bottom plate 22 is aligned with the rack channel 46 of the top plate 20 and the extension 42 of the top plate 20 is inserted into the slot 68 of the bottom plate 22 such that the ledge 44 of extension 42 slides under the undercut 70 of the bottom plate 22. The pinion lock 30 may be released from the pinion 26 with a tool so that translation of the top plate 20 relative to the bottom plate 22 is not arrested and the top plate 20 may be moved relative to the bottom plate 22. After the top plate 20 is connected to the bottom plate 22, the pinion pin 28 is inserted from the top surface of the top plate 20 into the central bore 82 of the pinion 26 until the ledge 29 of the pinion pin 26 abuts a ledge in the central bore 82. The distal end of the pinion pin 26 protrudes into the narrow opening 74 of the bottom plate 22. Bone fasteners 14 are inserted into the holes 32, 58 of the top plate 20 and bottom plate 22, respectively. The retention of the fasteners 14 relative to the plate 12 via one or more lock systems 16 will be described in greater detail below.

The top plate 20 is permitted to translate relative to the bottom plate 22 upon rotation of the pinion 26. An instrument is inserted into the socket 80 of the pinion 26 and when the pinion 26 is rotated in one direction, the teeth 78 of the pinion 26 cam against the projections 88 of the pinion lock 30 pushing the projections 88 outwardly while at the same time flexing the arms 84 of the pinion lock 30 also outwardly, thereby, releasing the pinion 26 into rotation and consecutive engagement with the teeth 76 on the rack 24. Rotation of the pinion 26 in one direction translates the elongated rack 24 that also moves the bottom plate 22 along with it relative to the top plate 20 into an expanded configuration. With a driving tool removed from the pinion 26, the position of the top plate 20 relative to the bottom plate 22 advantageously remains locked and fixed by the interlocked teeth 76, 78 of the rack 24 and pinion 26. No additional instrument, step or procedure is required to lock translation of the top plate 20 relative to the bottom plate 22. Various views of the expanded configuration of the plate 12 are depicted in FIGS. 28-31. Insertion of the tool into the pinion socket 80 and rotation of the pinion 26 in an opposite direction translates the rack 24 in the opposite direction translating the bottom plate 22 along with it relative to the top plate 20 into a closed configuration as shown in FIGS. 1, and 3-5. Hence, the length of the plate 12 and, therefore, the placement of the fasteners 14 can be finely adjusted as each click of the pinion increases the plate length by approximately 1-3 millimeters. This minute incremental expansion of the plate 12 advantageously provides for greater accuracy in the placement of fasteners 14 in, not only the upper vertebra, but also, in the lower vertebra resulting in greater controlled settling of the vertebral bodies and thereby enhancing the healing process. The fasteners 14 are threaded into bone and attached to the plate 12. Before the fasteners 14 are completely driven into the vertebral bodies, the plate length may be adjusted to be longer or smaller as needed. For example, the fasteners 14 at the proximal end of the plate 12 may be partially driven into the upper vertebral body followed by expanding or shortening the plate length as needed before partially driving the two fasteners 14 at the distal end of the plate 12 into the lower vertebral body. Then, the plate 12 length may be adjusted again, shortening or expanding the plate as needed for accurate positioning before driving the fasteners 12 in any order further into bone. The length adjustment may be repeated as needed until the fasteners 12 are in their final position inside the vertebral bodies and the plate 12 is completely attached. This intermittent adjustment of the plate length is easily accomplished by turning the pinion 26 with a driving tool. The driving tool may remain attached to the plate 12 via holes 56 for example so that the fine length adjustment may proceed incrementally as the fasteners 14 are driven into the bone.

The expandable bone plate 12 and fasteners 14 described above may further include one or more lock systems 16. Alternatively, one or more lock systems 16 according to the present invention may be used with any plate or construct where retention of screws to prevent back-out in situ is desired and not necessarily with the expandable plate described herein. Hence, the lock system 16 may be employed independently of the above-described expandable plate system. With reference back to FIGS. 1-5, each lock system 16 includes an actuator 100 coupled to the plate 12 and operably connected with two or more fastener locks 102. The fastener locks 102 are connected to the plate 12 with a lock pin 104. Two lock systems 16 are shown in FIGS. 1-5. One lock system 16 is located at the proximal end of the plate 12 and configured to lock the two fasteners 14 located in plate holes 32 at the proximal end and a second lock system 16 is located at the distal end of the plate 12 and configured to lock the two fasteners 14 located in plate holes 58 at the distal end of the plate 12. Each lock system 16 is located between two adjacent fasteners 14 located in two adjacent plate holes and configured to simultaneously lock the two adjacent fasteners 14. However, the invention is not so limited and a single lock system 16 may be easily modified and configured to simultaneously lock one or more fasteners 14 in situ.

Figure 32:
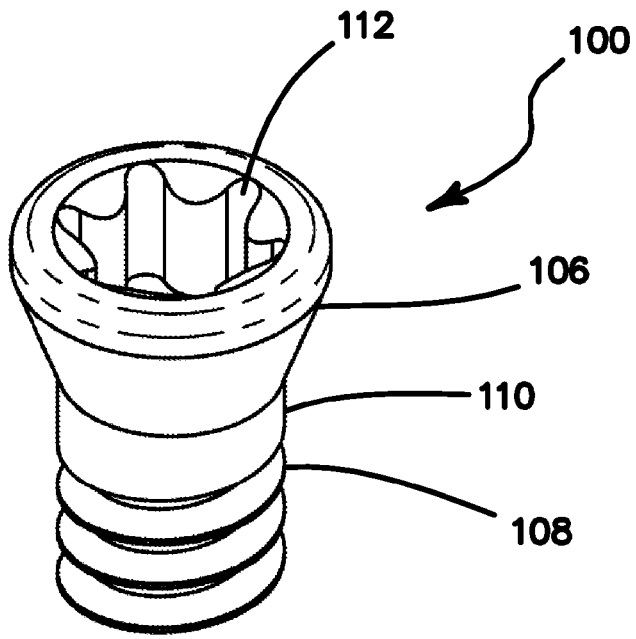
FIG. 32 is a top perspective view of an actuator according to the present invention.
Figure 33:
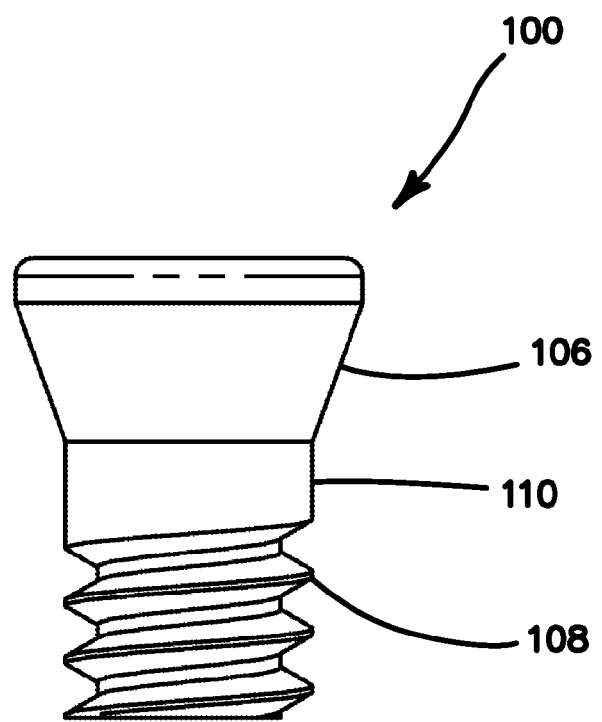
FIG. 33 is a side elevational view of an actuator according to the present invention.

Turning now to FIGS. 32-33, an actuator 100 of a lock system 16 according to the present invention will now be described. The actuator 100 is configured as a screw and includes a head 106 interconnected to a threaded shank 108 by a neck 110. The head 106 has a lateral dimension that is larger than the lateral dimension of the shank 108. At the proximal end of the head 106, a socket 112 is formed and configured to engage with an actuator driving tool to rotate the actuator 100 relative to the plate 12. A substantially hexagonal, daisy-shaped socket 112 is shown in FIG. 32; however the socket 112 can be of any shape that allows an instrument to rotate the actuator 100. The outer surface of the head 106 is tapered or angled toward the shank. In particular, the head 106 includes a lateral dimension that decreases distally with progressively distal radial cross-sections of the head 106. In another variation, the head 106 of the actuator 100 has a frustoconical shape with the radial cross-section decreasing toward the distal end of the head 106. The shank 108 is sized and configured to thread into the actuator apertures 40, 66 in the plate 12.

Figure 38:
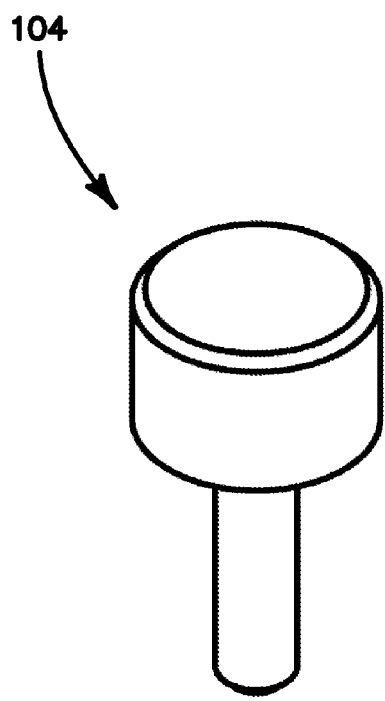
FIG. 38 is a top perspective view of a lock pin according to the present invention.

Turning now to FIGS. 34-37, the fastener locks 102 will now be described in detail. Each fastener lock 102 is substantially wishbone-shaped or Y-shaped having two arms 114 that interconnect at the proximal end 116. Each arm 114 comprises an outwardly angled segment 118 that is angled with respect to a longitudinal segment 120. The angled segments 118 may be bowed or curved as shown in FIGS. 34-35. An obtuse angle is defined between the longitudinal segment 120 and one of the angled segments 118 to define a Y-shaped fastener lock 102. A longitudinal slot 122 with an opening at the distal end extends toward the proximal end 116 along the longitudinal axis. The slot 122 is located between the two arms 114 in between the longitudinal segments 120. The proximal end of the slot 122 terminates at circular opening. The slot 122 provides the fastener lock 114 with added resiliency for the arms 114 such that the arms 114 may flex outwardly under force of the actuator 100 and spring back to their normal undeflected original condition. Each fastener lock 102 comprises two L-shaped segments connected to each other at the proximal end 116 with the longitudinal segments 120 located adjacent to each other opposite the slot 122 and an obtuse angle is formed between the longitudinal segment 120 and angled segment 118 of each L-shaped segment. Each arm 114 has an actuator-facing surface 124 and a fastener-facing surface 126. The actuator-facing surfaces 124 face toward the midline or longitudinal axis of the fastener lock 102 whereas the fastener-facing surfaces 126 face outwardly or away from the midline or longitudinal axis. The actuator and fastener facing surfaces 124, 126 are curved or convex and interconnect with a substantially planar top surface and a substantially planar bottom surface that are substantially parallel to each other. The fastener locks 102 are stackable one on top of each other and three fastener locks 102 are shown stacked on top of each other in a single lock system 16; however, one or more and, preferably, two or more fastener locks 102 may be employed per lock system 16. A lock pin 104 that is shown in FIG. 38 is provided and employed to connect the two or more stacked fastener locks 102 to the plate 12. In particular, the fastener locks 102 are stacked in the lock-receiving location 34 of the top plate 20 such that circular openings of each fastener lock 102 are aligned with each other and with the pin aperture 38. The lock pin 104 is then passed through the circular openings in the fastener locks 102 and into the pin aperture 38 to connect the fastener locks 102 to the plate 12. Although, three locks 102 are described, a single lock having the characteristics of two or more fastener locks 102 may be employed. The fastener locks 102 are connected to the plate 12 such that the arms 114 face the actuator aperture 40. The actuator 100 is inserted into the actuator aperture 40 and threaded downwardly into the plate 12 to connect the actuator 100 to the plate 12. Because the lock receiving locations 34, 60 of the plate 12 are recessed the actuator 100, fastener locks 102 and lock pins reside beneath the top surface of the plate 12 such that they do not protrude beyond the top surface of the plate 12 in order to maintain a low profile for the plate 12.

Fastener locks 102 are also connected to the distal end of the plate 12. In particular, in the case where a top plate 20 and a bottom plate 22 are employed, the fastener locks 102 are also stacked in the lock receiving location 60 of the bottom plate 22 such that circular openings of each fastener lock 102 are aligned with each other and with the pin aperture 64 of the bottom plate 22. The lock pin 104 is then passed through the circular openings in the fastener locks 102 and into the pin aperture 64 to connect the fastener locks 102 to the plate 12. The fastener locks 102 are connected to the plate 12 such that the arms 114 face the actuator aperture 66. An actuator 100 is inserted into the actuator aperture 40 and threaded downwardly into the plate 12 to connect the actuator 100 to the plate 12. The distance of the head 106 from the base surface 36 of the top plate 32 or height can be adjusted by threading the actuator 100 up or down into the plate 12 such that outer surface of the head 106 contacts the actuator facing surfaces 124 to lock or unlock the fasteners 14 as desired. An actuator 100 is inserted into the bottom plate 22 in the same manner. Advantageously, the head 106 of one actuator 100 contacts the actuator surfaces 124 of both arms 114 of the one or more locks 102 simultaneously allowing the actuator 100 to move or flex both arms 114 simultaneously toward fastener receiving holes 32, 58 of one or more locks 102. Hence, two fasteners 14 are locked or unlocked at the same time.

Figure 39:
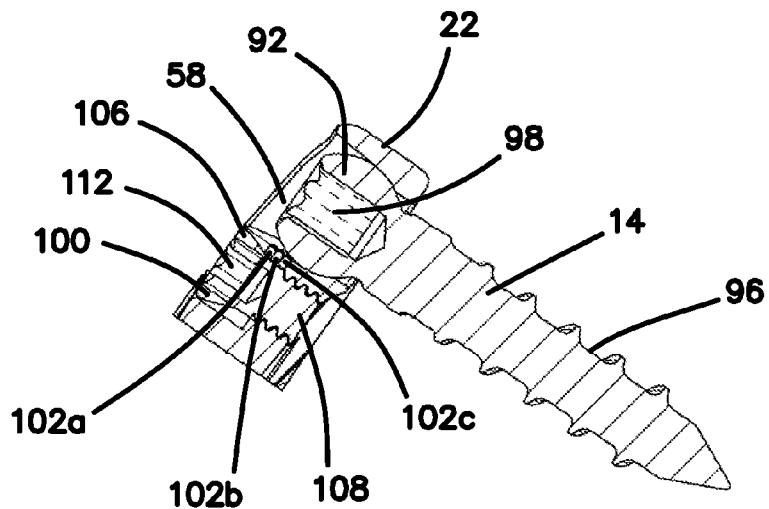
FIG. 39 is a cross-sectional view taken along line 39-39 of FIG. 3 of a bone plate system in an unlocked configuration according to the present invention.
Figure 40:
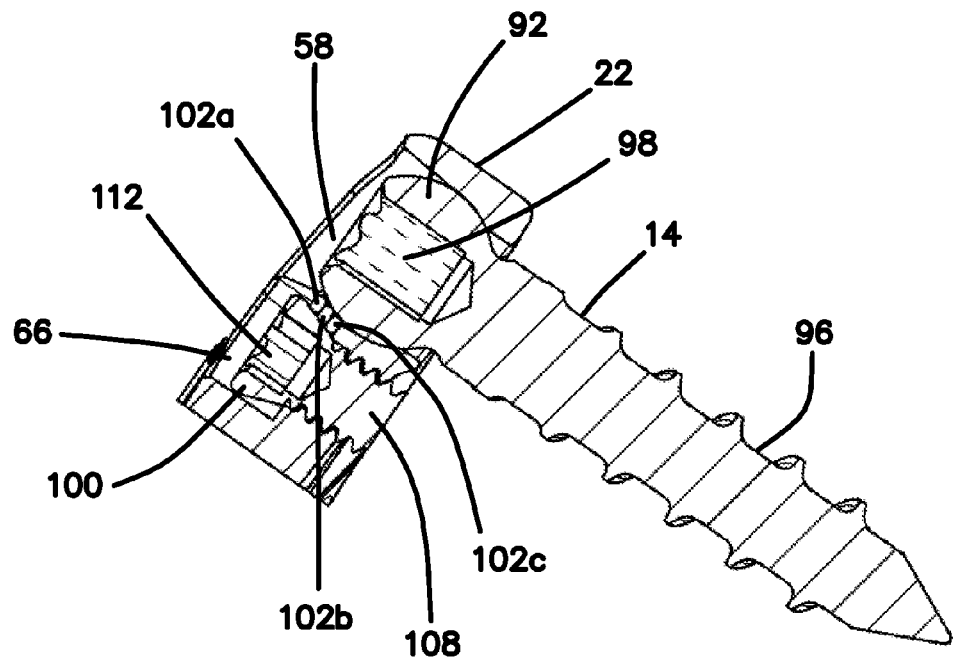
FIG. 40 is a cross-sectional view taken along line 39-39 of FIG. 3 of a bone plate system in a locked configuration according to the present invention.

With the plate 12 assembled and attached to bone in a final position, that is, the one or more fastener 14 at the proximal end of the plate 12 is attached to an upper vertebra and the one or more fastener 14 at the distal end of the plate 12 is attached to a lower vertebra, the lock systems 16 at each end of the plate 12 are activated by inserting a driving tool into the socket 112 of the actuator 100 and rotating to thread the actuator 100 downwardly into the plate 12 reducing the distance between of the top surface of the actuator 100 and the recessed base surface of the plate 12. As described above, the head 92 of a fastener 14 has a shape, the top of which is delimited by a top plane intersecting the shape. In one variation, the shape of the head is spherical and the top plane is parallel to a plane containing the diameter. As such, the top plane defines a circular cross-section of the sphere. In one variation, the top plane is perpendicular to the longitudinal axis of the fastener 14; however, the invention is not so limited. In another variation, the top plane defines a shape having a length that is shorter than the longest length of any cross-section of the shape. In one variation, the shape of the head is spherical and the top plane is parallel to a plane containing the diameter. Hence, the top plane has a circular cross-sectional shape having a diameter that is smaller than the diameter of the sphere. The aperture receiving holes 32, 58 are configured to seat the fastener head 92 in the typical fashion in which the elongated shank 96 protrudes outwardly from the bottom surface of the plate 12 and such that the fastener 14 is capable of angulating with respect to the plate 12. In one variation, the fastener 14 angulates polyaxially with respect to the plate 12. With reference now to FIG. 39, a fastener 14 is shown adjacent to an actuator 100 and three stacked fastener locks 102a, 102b, 102c in an unlocked configuration in which the fastener facing surfaces 126 of the two proximal locks 102a, 102b are not in contact with the head 92 and the distal-most lock 102c is shown to be in contact with fastener head 92. Even though the distal-most lock 102c is in contact with the fastener head 92, in one variation it does not interfere or minimally interferes with the translation of the fastener 14 into and out of the plate 12 in the unlocked configuration. In another variation, the distal-most lock 102c does not contact the fastener head 14. And, in another variation, any one or more of the locks 102 may contact the head 92 of the fastener 14 and not interfere or only minimally interfere with the translation of the fastener 14 into and out of the plate 12 in an unlocked configuration. As the actuator 100 is threaded downwardly into the plate 12, the outer surface of the actuator 100 that extends outwardly from the longitudinal axis of the actuator 100 will first contact the proximal-most fastener lock 102a. The user will continue to advance the actuator 100 into the plate 12 and the outer surface of the actuator 100 will contact or cam against the next fastener lock 102b and so on. With continued advancement of the actuator 100 into the plate 12, the outer surface of the actuator 100 will consecutively engage each fastener lock 102 from the proximal lock 102a to the distal lock 102c. As a result of the tapered or narrowing outer dimension of the outer surface toward the distal end of the actuator 100 and widening outer dimension of the outer surface toward the proximal end of the actuator 100 and its resultant progressive engagement with successive fastener locks 102 as the actuator 100 moves in the distal direction, the locking system 16 provides a graduated locking mechanism. From an unlocked configuration, such as the configuration depicted in FIG. 39, incremental translation of the actuator 100 into the plate 12 will result in an intermediate locked configuration in which at least one of the fastener locks 102 is above the top plane of the head 92 or is in contact with the head 92 of the fastener 14 at a location above a planar cross-section of the head 92 having a longest length in the cross-section. For example, in the case of a spherical head 92, the cross-section of the head 92 having the longest length will be the planar cross-section that contains the center of the sphere and contact of the at least one fastener lock 102 with the outer surface of the head 92 will be above the center point of the sphere. In such an intermediate locked configuration, the at least one fastener lock 102 in contact with the outer surface of the head 92 at a location above the center will provide anti-back out protection for the fastener 14 relative to the plate 12 in situ while still permitting the fastener 14 to angulate with respect to the plate 12. From the intermediate locked configuration just described, continued incremental translation of the actuator 100 into the plate 12 will sequentially move all of the fastener locks 102 into contact with the fastener head 92 as shown in FIG. 40 which depicts a locked configuration. In FIG. 40, fastener locks 102a, 102b, 102c are in contact with the fastener head 92. In the locked configuration, the angulation of the fastener 14 relative to the plate 12 is arrested in addition to back out protection being provided. If the actuator 100 is rotated in the opposite direction, the locking system 16 will move sequentially from the locked configuration to the intermediate locked configuration to the unlocked configuration. In the unlocked configuration the fastener 14 can be removed from the fastener receiving hole and no or little resistance is provided to retain the fastener 14 from backing out of the fastener receiving hole. In the intermediate locked configuration, the fastener 14 is permitted to angulate inside the fastener receiving hole but is not permitted to move proximally out of the plate 12; hence, back out protection is provided to the fastener 14. In the locked configuration, in addition to the fastener being prevented from backing out of the plate 12, the fastener is fixed with respect to the plate 12 and arrested from angulating with respect to the plate 12. The actuator 100 will contact the actuator facing surfaces 124 of the arms 114 of the fastener lock 102 deflecting the arms 114 outwardly away from the midline of the fastener lock 102 with distal translation of the outer surface of the actuator 100 relative to the plate 12 bringing the fastener facing surfaces 126 of the arms 114 into contact with the outer surface of the fastener head 92. The arms 114 are flexed such that reverse rotation of the actuator 100 permits the arms 114 to spring back or otherwise move inwardly toward the actuator 100 to uncover the fastener 14 or otherwise permit the fastener 14 to translate proximally out of the plate 12. In another variation, the entire fastener lock 102 translates towards the fastener 14 relative to the plate 12. And, in another variation, the entire fastener lock 102 translates relative to the plate and also the arms 114 are flexed outwardly with continued distal translation of the actuator 100 relative to the plate 12. Reverse rotation of the actuator 100 permits the flexed arms 114 to spring back away from the fastener head 92 and proximal translation of the fastener 14 will result in the fastener head 92 camming against the lock 102 moving the entire lock 102 out of the way for removal of the fastener in the proximal direction. The multiple stacked fastener locks 102 and their sequential deployment advantageously permit the locks 102 to conform closely to the geometry of the fastener head 92 and come into contact with a greater surface area of the head and as a result apply greater friction regardless of the position or angulation of the fastener 14. Unlike non-multiple or unitary locks that must have a predetermined shape that conforms to a greater surface area of the head and to do so at even at any angle of the fastener, the locks of the present invention need only conform individually to a narrow surface area of the fastener-facing surface defined between the top surface and the bottom surface of fastener lock 102. Furthermore, the graduated locking system 16 of the present invention advantageously permits the user to readjust the placement of the plate 12 on the bone with the locking system 16 in an intermediate locked configuration without the risk or trouble of the fastener 14 backing out during the readjustment.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:

1. A bone plate system, comprising:
  a plate having at least one hole configured to receive a bone fastener for attaching the plate to bone; the plate having a top surface and a bottom surface interconnected by a side surface;
  an actuator located adjacent to the at least one hole; the actuator having a proximal end, a distal end, a longitudinal axis and an outer surface; in a cross section of the actuator taken perpendicular to the longitudinal axis, the outer surface of the actuator defines a shape having a length defined from its center to its perimeter; the length increases in progressively proximal cross sections perpendicular to the longitudinal axis, the actuator being connected to the plate such that the actuator moves relative to the top surface of the plate;
  at least two locks stacked on top of each other and located between the actuator and the at least one hole; each lock having at least one actuator-facing surface and at least one fastener-facing surface; the at least two locks being coupled to the plate such that at least a portion of each lock is movable relative to the plate, the actuator-facing surface faces the actuator, and the fastener-facing surface faces the at least one hole;
  wherein movement of the actuator in a first direction relative to the plate moves at least a portion of each lock laterally closer to the at least one hole and moves the at least two locks consecutively with respect each other.

2. The bone plate system of claim 1 wherein each lock moves consecutively and laterally closer to the actuator with movement of the actuator in a second direction.

3. The bone plate system of claim 1 further includes at least one fastener having a head at the proximal end; a fastener being disposed inside at least one hole of the plate; the head having a center;
  wherein movement of the actuator in the first direction defines a first locked configuration in which at least one of the stacked locks contacts the head at a plane above the center of the head to resist movement of the fastener proximally relative to the plate.

4. The bone plate system of claim 3 wherein the fastener disposed inside the at least one hole of the plate angulates relative to the plate in an unlocked configuration and in the first locked configuration; and
  wherein further movement of the actuator in the first direction defines a second locked configuration in which at least one of the stacked locks contacts the head at a plane above the center of the head to resist movement of the fastener proximally relative to the plate and at least one of the stacked locks contacts the head at a plane containing the center of the head or at a plane below the center of the head to fix the angulation of the fastener relative to the plate.

5. The bone plate system of claim 1 comprising two adjacent holes at one end of the plate; each lock having two actuator-facing surfaces facing the actuator and two fastener-facing surfaces facing the two holes;
  wherein movement of the actuator in the first direction moves both fastener-facing surfaces of each lock simultaneously toward the two holes.

6. The bone plate system of claim 5 wherein both actuator-facing surfaces of each lock move closer to the actuator with movement of the actuator in the second direction.

7. The bone plate system of claim 5 wherein each lock is Y-shaped.

8. The bone plate system of claim 1 wherein the actuator rotates with respect to the plate.

9. The bone plate system of claim 1 wherein the actuator translates into and out of the plate.

10. The bone plate system of claim 9 wherein the actuator includes a head at the proximal end having a frustoconical outer surface.

11. The bone plate system of claim 10 wherein actuator includes a threaded shank at the distal end.

12. A bone plate system, comprising:
  a plate having at least one hole configured to receive a bone fastener for attaching the plate to bone; the plate having a top surface and a bottom surface interconnected by a side surface;
  at least one fastener having a head at a proximal end and a bone-engaging portion distal to the head; the bone-engaging portion extending to a distal end; a fastener being disposed inside at least one hole of the plate such that the head is substantially seated inside the hole and the bone-engaging portion extends from the bottom surface of the plate;
  a locking system connected to the plate and including:
    an actuator connected to the plate and located adjacent to the at least one hole;
    a lock having at least one fastener-facing surface and at least one actuator facing surface; the lock being located between the actuator and the inserted fastener such that the actuator-facing surface faces the actuator and the fastener-facing surface faces the fastener;
    an unlocked configuration in which the fastener is removable from the hole in a proximal direction and permitted to angulate with respect to the plate;
    a first locked configuration in which the fastener is prevented from being removed from the hole in a proximal direction and is permitted to angulate with respect to the plate; and
    a second locked configuration in which the angulation of the fastener with respect to the plate is fixed and the fastener is prevented from being removed from the hole in a proximal direction;
    wherein movement of the actuator in the vertical direction with respect to the plate moves the at least one fastener-facing surface in a lateral direction.

13. The bone plate system of claim 12 wherein the actuator includes a head at the proximal end having a cross-sectional shape taken perpendicular to the longitudinal axis of the actuator that decreases with progressive distal cross-sections of the actuator head.

14. A bone plate system, comprising:
a plate having at least one hole configured to receive a bone fastener for attaching the plate to bone; the plate having a top surface and a bottom surface interconnected by a side surface;
at least one fastener having a head at a proximal end and a bone-engaging portion distal to the head; the bone-engaging portion extending to a distal end; a fastener being disposed inside at least one hole of the plate such that the head is substantially seated inside the hole and the bone-engaging portion extends from the bottom surface of the plate;
a locking system connected to the plate and including:
an actuator located adjacent to the at least one hole; the actuator having a proximal end, a distal end, a longitudinal axis and an outer surface; the actuator being connected to the plate such that the actuator moves relative to the top surface of the plate; and
a lock having at least two fastener-facing surfaces and at least one actuator-facing surface; the lock being located between the actuator and the inserted fastener such that the actuator-facing surface faces the actuator and the fastener-facing surface faces the fastener; the at least two fastener-facing surfaces being independently movable by the actuator to sequentially and laterally translate the fastener-facing surfaces; wherein movement of the actuator moves the at least two fastener-facing surfaces laterally between:
an unlocked configuration in which the fastener is removable from the hole in a proximal direction and permitted to angulate with respect to the plate;
a first locked configuration in which the fastener is prevented from being removed from the hole in a proximal direction and is permitted to angulate with respect to the plate; and
a second locked configuration in which the angulation of the fastener with respect to the plate is fixed and the fastener is prevented from being removed from the hole in a proximal direction.

15. A bone plate system, comprising:
a plate having at least one hole configured to receive a bone fastener for attaching the plate to bone; the plate having a top surface and a bottom surface interconnected by a side surface;
at least one fastener having a head at a proximal end and a bone-engaging portion distal to the head; the bone-engaging portion extending to a distal end; a fastener being disposed inside at least one hole of the plate such that the head is substantially seated inside the hole and the bone-engaging portion extends from the bottom surface of the plate;
a locking system connected to the plate and including:
an unlocked configuration in which the fastener is removable from the hole in a proximal direction and permitted to angulate with respect to the plate;
a first locked configuration in which the fastener is prevented from being removed from the hole in a proximal direction and is permitted to angulate with respect to the plate; and
a second locked configuration in which the angulation of the fastener with respect to the plate is fixed and the fastener is prevented from being removed from the hole in a proximal direction;
wherein the locking system further includes:
an actuator located adjacent to the at least one hole; the actuator having a proximal end, a distal end, a longitudinal axis and an outer surface; the actuator being connected to the plate such that the actuator moves relative to the top surface of the plate; and
three locks, each having a fastener-facing surface and an actuator-facing surface; the three locks being located between the actuator and the inserted fastener such that the actuator-facing surfaces face the actuator and the fastener-facing surfaces face the fastener; each lock being independently movable by the actuator to sequentially contact the head of the fastener;
wherein movement of the actuator moves the locks laterally between the unlocked configuration, first locked configuration, and second locked configuration.

16. A bone plate system, comprising:
a plate having at least one hole configured to receive a bone fastener for attaching the plate to bone; the plate having a top surface and a bottom surface interconnected by a side surface;
at least one fastener having a head at a proximal end and a bone-engaging portion distal to the head; the bone-engaging portion extending to a distal end; a fastener being disposed inside at least one hole of the plate such that the head is substantially seated inside the hole and the bone-engaging portion extends from the bottom surface of the plate;
a locking system connected to the plate and including:
an unlocked configuration in which the fastener is removable from the hole in a proximal direction and permitted to angulate with respect to the plate;
a first locked configuration in which the fastener is prevented from being removed from the hole in a proximal direction and is permitted to angulate with respect to the plate; and
a second locked configuration in which the angulation of the fastener with respect to the plate is fixed and the fastener is prevented from being removed from the hole in a proximal direction;
wherein the locking system includes:
an actuator located adjacent to the at least one hole; the actuator having a proximal end, a distal end, a longitudinal axis and an outer surface; the actuator being connected to the plate such that the actuator moves relative to the top surface of the plate; and
a lock having at least one fastener-facing surface and at least one actuator-facing surface; the lock being located between the actuator and the inserted fastener such that the actuator-facing surface faces the actuator and the fastener-facing surface faces the fastener;
wherein movement of the actuator moves the at least one fastener-facing surface laterally between the unlocked configuration, first locked configuration, and second locked configuration; and
wherein the actuator includes a head at the proximal end having a cross-sectional shape taken perpendicular to the longitudinal axis of the actuator that decreases with progressive distal cross-sections of the actuator head.

17. The bone plate system, comprising:
a first plate having at least one hole configured to receive a bone fastener; the first plate having a top surface and a bottom surface interconnected by a side surface; the first plate having a distal extension with an aperture extending between the top surface and the bottom surface;
a second plate having at least one hole configured to receive a bone fastener; the second plate having a top surface and a bottom surface interconnected by a side surface; the second plate having a proximal slot configured to receive the distal extension of the first plate;

an elongated rack having an outer surface; the elongated rack having teeth formed on the outer surface; the rack being located between the first plate and the second plate;

a pinion having a proximal end and a distal end interconnected by an outer surface; the pinion includes teeth formed on the outer surface and a central bore extending between an opening at the proximal end and an opening at the distal end; the pinion being located between the first plate and the second plate; the opening at the proximal end defining a socket configured to receive a driving instrument;

a pinion pin located inside the central bore of the pinion;

a lock located between the first plate and the second plate; the lock having at least one projection extending toward the teeth of the pinion to arrest rotation of the pinion in either direction of rotation of the pinion;

wherein the first plate is connected to the second plate by the rack and pinion such that the first plate is longitudinally movable with respect to the second plate by rotation of the pinion to change the overall longitudinal length of the plate system;

wherein rotation of the pinion in one direction increases the length of the plate system and rotation of the pinion in an opposite direction decreases the length of the plate system; and wherein the length of the plate system is always locked when the pinion is not rotating.

18. The bone plate system of claim 17 wherein the second plate has an elongated opening and the pinion pin is inserted into the central bore of the pinion and into the elongated opening of the second plate.

19. The bone plate system of claim 17 further including a locking system that locks the angulation of a fastener inserted into the at least one hole and resists the fastener from backing out of the hole.

* * * * *